United States Patent
Haugland et al.

(10) Patent No.: US 9,150,922 B2
(45) Date of Patent: Oct. 6, 2015

(54) CYANINE COMPOUNDS AND THEIR APPLICATION AS QUENCHING COMPOUNDS

(71) Applicant: LIFE TECHNOLOGIES CORPORATION, Carlsbad, CA (US)

(72) Inventors: Rosaria Haugland, Eugene, OR (US); Ching-Ying Cheung, San Ramon, CA (US); Stephen Yue, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/109,475

(22) Filed: Dec. 17, 2013

(65) Prior Publication Data

US 2014/0295437 A1 Oct. 2, 2014

Related U.S. Application Data

(63) Continuation of application No. 13/005,002, filed on Jan. 12, 2011, now abandoned, which is a continuation of application No. 11/782,244, filed on Jul. 24, 2007, now abandoned, which is a continuation of application No. 10/916,822, filed on Aug. 11, 2004, now Pat. No. 7,271,265.

(60) Provisional application No. 60/494,448, filed on Aug. 11, 2003.

(51) Int. Cl.
| | | |
|---|---|---|
| C07D 401/04 | (2006.01) | |
| C07D 209/14 | (2006.01) | |
| C12Q 1/68 | (2006.01) | |
| C07D 209/12 | (2006.01) | |
| C07D 209/24 | (2006.01) | |
| C09B 23/12 | (2006.01) | |

(52) U.S. Cl.
CPC ............ *C12Q 1/6876* (2013.01); *C07D 209/12* (2013.01); *C07D 209/14* (2013.01); *C07D 209/24* (2013.01); *C07D 401/04* (2013.01); *C09B 23/12* (2013.01)

(58) Field of Classification Search
CPC ........................... C07D 401/14; C07D 209/14
See application file for complete search history.

(56) References Cited

U.S. PATENT DOCUMENTS

| | | | |
|---|---|---|---|
| 3,730,711 A | 5/1973 | Ono et al. | |
| 4,210,591 A | 7/1980 | Burri | |
| 4,520,110 A | 5/1985 | Stryer et al. | |
| 4,542,104 A | 9/1985 | Stryer et al. | |
| 4,603,209 A | 7/1986 | Tsien et al. | |
| 4,711,955 A | 12/1987 | Ward et al. | |
| 4,774,339 A | 9/1988 | Haugland et al. | |
| 4,810,636 A | 3/1989 | Corey et al. | |
| 4,812,409 A | 3/1989 | Babb et al. | |
| 4,849,362 A | 7/1989 | DeMarinis et al. | |
| 4,859,582 A | 8/1989 | Stryer et al. | |
| 4,883,867 A | 11/1989 | Lee et al. | |
| 4,945,171 A | 7/1990 | Haugland et al. | |
| 4,957,870 A | 9/1990 | Lee et al. | |
| 5,047,519 A | 9/1991 | Hobbs et al. | |
| 5,055,556 A | 10/1991 | Stryer et al. | |
| 5,130,227 A | 7/1992 | Wade et al. | |
| 5,132,432 A | 7/1992 | Haugland et al. | |
| 5,187,288 A | 2/1993 | Kang et al. | |
| 5,227,487 A | 7/1993 | Haugland et al. | |
| 5,242,805 A | 9/1993 | Naleway et al. | |
| 5,248,782 A | 9/1993 | Haugland et al. | |
| 5,268,486 A | 12/1993 | Waggoner et al. | |

(Continued)

FOREIGN PATENT DOCUMENTS

| | | |
|---|---|---|
| EP | 0745690 | 12/1996 |
| WO | WO 97/39064 | 10/1997 |

OTHER PUBLICATIONS

Allmann, et al. "Konformationsanalyse von Polymethinen I, Erstmaliger Nachweis von di-, tri- und all-cis-Konformationen bei sterisch gehinderten Trimethincyaninen (Carbocyaninen) der Indolin- und Benzothiazolreihe" Angew. Chem. Suppl. 1983, 1147-1175.*

(Continued)

*Primary Examiner* — Joseph Kosack
(74) *Attorney, Agent, or Firm* — Life Technologies Corporation

(57) ABSTRACT

The present invention provides methods and non-fluorescent carbocyanine quencher compounds having the general formula:

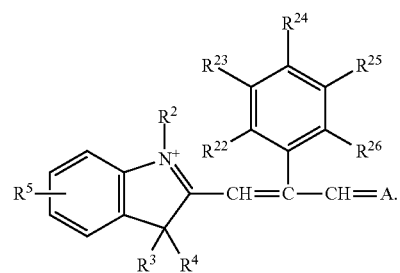

Wherein the A moiety is a substituted pyridinium, unsubstituted pyridinium, substituted quinolinium, unsubstituted quinolinium, substituted benzazolium, unsubstituted benzazolium, substituted indolinium, or substituted indolinium. The invention further provides luminescent donor molecule-quencher pairs and luminescent donor molecule-quencher-luminescent acceptor molecule conjugates wherein the quencher is a cyanine compound of the present invention. The energy transfer pairs are used to detect an analyte of interest in a sample.

14 Claims, 5 Drawing Sheets

(56) References Cited

U.S. PATENT DOCUMENTS

| | | |
|---|---|---|
| 5,274,113 A | 12/1993 | Kang et al. |
| 5,326,692 A | 7/1994 | Brinkley |
| 5,352,803 A | 10/1994 | Mattingly |
| 5,362,628 A | 11/1994 | Haugland et al. |
| 5,433,896 A | 7/1995 | Kang et al. |
| 5,436,134 A | 7/1995 | Haugland et al. |
| 5,442,045 A | 8/1995 | Haugland et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,534,416 A | 7/1996 | Millard et al. |
| 5,569,587 A | 10/1996 | Waggoner |
| 5,569,766 A | 10/1996 | Waggoner et al. |
| 5,573,904 A | 11/1996 | Mattingly |
| 5,573,909 A | 11/1996 | Singer et al. |
| 5,627,027 A | 5/1997 | Waggoner |
| 5,656,554 A | 8/1997 | Desai et al. |
| 5,658,751 A | 8/1997 | Yue et al. |
| 5,691,145 A | 11/1997 | Pitner et al. |
| 5,696,157 A | 12/1997 | Wang et al. |
| 5,714,327 A | 2/1998 | Houthoff et al. |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,847,162 A | 12/1998 | Lee et al. |
| 5,853,969 A | 12/1998 | Harada et al. |
| 5,863,727 A | 1/1999 | Lee et al. |
| 5,863,753 A | 1/1999 | Haugland et al. |
| 5,925,517 A | 7/1999 | Tyagi et al. |
| 5,945,526 A | 8/1999 | Lee et al. |
| 6,008,373 A | 12/1999 | Waggoner et al. |
| 6,008,379 A | 12/1999 | Benson et al. |
| 6,017,712 A | 1/2000 | Lee et al. |
| 6,025,505 A | 2/2000 | Lee et al. |
| 6,027,709 A | 2/2000 | Little et al. |
| 6,048,982 A | 4/2000 | Waggoner et al. |
| 6,080,852 A | 6/2000 | Lee et al. |
| 6,103,476 A | 8/2000 | Tyagi et al. |
| 6,114,350 A | 9/2000 | Randall et al. |
| 6,130,101 A | 10/2000 | Mao et al. |
| 6,140,494 A | 10/2000 | Hamilton et al. |
| 6,162,931 A | 12/2000 | Gee et al. |
| 6,184,379 B1 | 2/2001 | Josel et al. |
| 6,197,956 B1 | 3/2001 | Randall et al. |
| 6,204,389 B1 | 3/2001 | Randall et al. |
| 6,221,606 B1 | 4/2001 | Benson et al. |
| 6,224,644 B1 | 5/2001 | Randall et al. |
| 6,225,050 B1 | 5/2001 | Waggoner |
| 6,229,055 B1 | 5/2001 | Klaubert et al. |
| 6,323,337 B1 | 11/2001 | Singer et al. |
| 6,335,440 B1 | 1/2002 | Lee et al. |
| 6,348,596 B1 | 2/2002 | Lee et al. |
| 6,348,599 B1 | 2/2002 | Cummins et al. |
| 6,358,684 B1 | 3/2002 | Lee |
| 6,372,445 B1 | 4/2002 | Davis et al. |
| 6,399,392 B1 | 6/2002 | Haugland et al. |
| 6,403,807 B1 | 6/2002 | Singh et al. |
| 6,562,632 B1 | 5/2003 | Szalecki et al. |
| 6,664,047 B1 | 12/2003 | Haugland et al. |
| 6,716,979 B2 | 4/2004 | Diwu et al. |
| 6,974,873 B2 | 12/2005 | Leung et al. |
| 6,977,305 B2 | 12/2005 | Leung et al. |
| 7,271,265 B2 * | 9/2007 | Haugland et al. .......... 546/277.4 |
| 2002/0064794 A1 | 5/2002 | Leung et al. |
| 2002/0077487 A1 | 6/2002 | Leung et al. |
| 2011/0105362 A1 | 5/2011 | Haugland et al. |

OTHER PUBLICATIONS

Schobel, et al. "New Donor-Acceptor Pair for Fluorescent Immunoassays by Energy Transfer" Bioconjugate Chem. 1999, 10, 1107-1114.*

Haughland, R.P. "Handbook of Fluorescent Probes and Research Products" Molecular Probes, 2002.*

Allmann, et al., "Konformationsanalyse von Polymethinen I, Erstmaliger Nachweis von di-, tri- und all-cis-Konformationen bei sterisch gehinderten Trimethincyaninen (Carbocyaninen) der Indolin- und Benzothiazolreihe", *Angewandte Chemie International Edition in German*, vol. 22, Issue Supplement 11,, Nov. 1983, 1147-1175.

Beebe, et al., "A continuous fluorimetric assay for tail-specific protease", *Analytical Biochemistry*, vol. 263, Issue 1,, Oct. 1, 1998, 51-56.

Beekman, et al., "Highly increased levels of active stromelysin in rheumatoid synovial fluid determined by a selective fluorogenic assay", *FEBS Letters*, vol. 418, Issue 3, Dec. 1, 1997, 305-309.

Beekman, B. et al., "Convenient fluorometric assay for matrix metalloproteinase activity and its application in biological media", *FEBS Letters*, 390(2), 1996, 221-225.

Brinkley, Michael , "A Brief Survey of Methods for Preparing Protein Conjugates with Dyes, Haptens, and Cross-Linking Reagents", *Bioconjugate Chemistry*, vol. 3, Issue 1, 1992, pp. 2-13.

Browning, et al., "Studies on the Differing Effects of the Tumor Necrosis Factor and Lymphotoxin on the Growth of Several Human Tumor Lines", *Journal of Immunology*, vol. 143, Issue 6, 1989, pp. 1859-1867.

Dos Remedios, Cristobal G. et al., "Fluorescence Resonance Energy Transfer Spectroscopy is a Reliable "Ruler" for Measuring Structural Changes in Proteins", *Journal of Structural Biology*, vol. 115, 1995, pp/ 175-185.

Furniss, Brian S. et al., "Resolution of Racemates", *Vogel's Textbook of Practical Organic Chemistry*, Fifth Ed, Longman Group UK Ltd., Essex, 1989, 809-823.

Georgi, Ann et al., "Detection of Individual Fluorescently Labeled Reovirions in Living Cells", *Proceedings of the National Academy of Sciences (PNAS)*, vol. 87, 1990, 6579-6583.

Haugland, Richard P. , "Molecular Probes Handbook of Fluorescent Probes and Research Products", *9th Edition, 2002 (CD-Rom Format), Molecular Probes*, 2002.

Haugland, Rosaria P. , "Coupling of monoclonal antibodies with fluorophores", *Methods in Molecular Biology*, Monoclonal Antibody Protocols, vol. 45, 1995, pp. 205-243.

Heller, A. , "Electrical Wiring of Redox Enzymes", *Acc. Chem. Res.*, vol. 23, No. 5, 1990, 128-134.

Holskin, B. P. et al., "A continuous fluorescence-based assay of human *cytomegalovirus* protease using a peptide substrate", *Analytical Biochemistry*, vol. 226, 1995, 148-55.

Joshi, Saroj et al., "ATP Synthase Complex from Bovine Heart Mitochondria", *J. Biol. Chem.*, vol. 265(24), 1990, pp. 14518-14525.

Jung, Stephanie M. et al., "Crosslinking of platelet glycoprotein lb by N-succinimidyl(4-azidophenyldithio)propionate and 3,3'-dithiobis-(sulfosuccinimidyl propionate)", *Biochimica et Biophysica Acta*, vol. 761, Iss. 2, 1983, pp. 152-162.

Matayoshi, et al., "Novel Fluoregenic Substrates for Assaying Retroviral Proteases by Resonance Energy Transfer", *Science*, vol. 247, Feb. 23, 1990, pp. 954-958.

Morrison, Larry E. , "Detection of Energy Transfer and Fluorescence Quenching", *Nonisotopic DNA Probe Techniques*, L. Kricka, ed., 1992, 311-352.

Park, Linda S. et al., "Characterization of the Cell Surface Receptor for a Multi-Lineage Colony-Stimulationg Factor (CSF-2alpha)*", *J. Biol. Chem., vol. 261, No. 1*, 1986, 205-210.

Pennington, M. W. et al., "Synthesis of fluorogenic interleukin-1 beta converting enzyme substrate based on resonance energy transfer", *Pep. Res*, vol. 7, No. 2, 1994, 72-76.

Przhiyalgovskaya, N. M. et al., "Carbocyanine Dyes with an O-hydroxyaryl Substituent in the Meso Position of the Polymethine Chain", *Translated from Khimiya Geterotsiklicheskikh Soedinenii*, No. 1, pp. 100-103, 1988, 83-86.

Sandler, Stanley R. et al., "Organic Functional Group Preparations", vol. 3, *New York: Academic Press*, 1972, 5-9.

Schobel, Uwe et al., "New Donor-Acceptor Pair for Fluorescent Immunoassys by Energy Transfer", *Bioconjugate Chem.*,vol. 10, Oct. 9, 1999, 1107-1114.

Selvin, Paul R. , "Fluorescence Resonance Energy Transfer", *Methods in Enzymology*, vol. 246, 1995, 300-334.

(56) References Cited

OTHER PUBLICATIONS

Spatola, et al., "Ch 5: Peptide Backbone Modifications: A Structure-Activity Analysis of Peptides Containing Amide Bond Surrogates, Conformational Constraints, and Rela", *Chemistry and Biochemistry of Amino Acids, Peptides and Proteins*, vol. 7, 1983, 267-357.

Tyagi, et al., "Molecular Beacons: Probes that Fluoresce upon Hybridization", *Nature Biotechnology*, vol. 14, No. 3, Mar. 1996, 303-308.

Tyagi, Sanjay et al., "Multicolor molecular beacons for allele discrimination", *Nature Biotechnology*, vol. 16, 1998, 49-53.

Wang, Q. M. et al., "Development of a conscious fluorescence assay for rhinovirus 14 3C protease using synthetic peptides", *Antiviral Chemistry & Chemotherapy*, vol. 8, No. 4, 1997, 303-310.

Wu, Pengguang et al., "Resonance Energy Transfer: Methods and Applications", *Analytical Biochemistry*, vol. 218, No. 1, 1994, 1-13.

Yoshimura, Akihiko et al., "Uncoating of Influenza Virus in Endosomes", *Journal of Virology*, vol. 51, No. 2, 1984, 497-504.

Zarling, David A. et al., "Mapping of Lymphocyte Surface Polypeptide Antigens by Chemical Cross-Linking with BSOCOES", *Journal of Immunology*, vol. 124, No. 2, 1980, 913-920.

\* cited by examiner

CYANINE COMPOUNDS AND THEIR APPLICATION AS QUENCHING COMPOUNDS

CROSS-REFERENCE TO RELATED APPLICATIONS

This application is a continuation of U.S. application Ser. No. 11/782,244, filed Jul. 24, 2007, which is a continuation of U.S. application Ser. No. 10/916,822, filed Aug. 11, 2004 (now U.S. Pat. No. 7,271,265), which claims priority to U.S. Provisional Application No. 60/494,448, filed Aug. 11, 2003, the disclosures of which are herein incorporated by reference.

FIELD OF THE INVENTION

The present invention relates to cyanine compounds that are efficient quenchers of luminescence. The invention has applications in the fields of molecular biology, immunology and fluorescence-based assays.

BACKGROUND OF THE INVENTION

Fluorescence Resonance Energy Transfer (FRET) is a process whereby a first fluorescent dye (the "donor" dye) is excited, typically by illumination, and transfers its absorbed energy to a second dye (the "acceptor" dye) that has a longer wavelength and therefore lower energy emission. Where the second dye is fluorescent, energy transfer results in fluorescence emission at the wavelength of the second dye. However, where the second dye is non-fluorescent, the absorbed energy does not result in fluorescence emission, and the fluorescence of the initial donor dye is said to be "quenched". The proximity of the donor and acceptor molecule and the overlap in spectra of the energy emitted by the donor and the absorption spectra of the acceptor molecule are critical for efficient energy transfer.

When the acceptor molecule is a quencher, the FRET pair can be used in assays to detect the interaction, assembly, cleavage, dissociation and conformation of proteins, nucleic acids and other biomolecules. This can be accomplished when the donor and acceptor are conjugated to different substances wherein the resulting signal is determined by the proximity of the donor and acceptor molecules. Cleavable conjugates are also widely used to detect proteases wherein the donor and acceptor are conjugated to the same substance and the appropriate protease cleaves a bond that changes the proximity of the donor and acceptor (U.S. Pat. Nos. 6,323,337; 6,348,596 and 6,399,392).

In addition, FRET is used in bioassays wherein it is beneficial to have energy emitted at a longer wavelength that does not interfere with the autofluorescence of the bioassay sample. Typically in these bioassays a FRET pair, commonly referred to as a tandem, is conjugated to an antibody or other ligand for the detection of an analyte. These tandem conjugates are also widely used with flow cytometers and confocal laser scanning microscopes that are equipped with separate epifluorescence filter sets wherein a larger Stokes shift is beneficial for multicolor applications. Phycobiliproteins are well known fluorescent proteins that are used as a donor conjugated to a protein such as an antibody wherein a xanthene based dye such as Texas Red (Molecular Probes, Inc.) or a cyanine dye is used as the acceptor (U.S. Pat. Nos. 4,859,582 and 4,542,104; RICHARD P. HAUGLAND, MOLECULAR PROBES HANDBOOK OF FLUORESCENT PROBES AND RESEARCH PRODUCTS; 9$^{th}$ edition, CD-ROM, 2002). In this way, with the Texas Red conjugate of R-phycoerythrin (R-PE), the resulting tandem conjugate can be excited at 488 nm using the widely available argon-ion laser and the energy is re-emitted at about 620 nm or longer after having been transferred to the acceptor dye. Importantly, this permits the simultaneous use of a second conjugate of R-PE that is not a tandem conjugate as a label for a different target. These tandem conjugates find wide use in bioassays; however, in systems that utilize flow cytometry the signal from the fluorescent protein is not fully transferred to the acceptor and therefore must be compensated for when determining multiple targets with labels that absorb and emit in the same range as the fluorescent protein. Thus, there is a need to reduce this compensation determining multiple targets in a sample using R-PE tandem conjugates.

The idea of using a quencher to form a ternary conjugate wherein the quencher compound accepts the residual energy of the R-PE donor compound goes against the current teaching and understanding of FRET. However, we have unexpectedly demonstrated that a compound absorbing in the emitting range of the R-PE can accept the residual fluorescense of the fluorescent protein. This unexpected improvement allows for detection of multiple targets using R-PE tandem conjugates by lowering the need for compensation. Ideally these compounds will be non-fluorescent, or essentially non-fluorescent, and will accept energy in the range that the donor emits the residual fluorescence.

The compounds of the instant invention represent a new and highly useful class of non-fluorescent energy acceptors, including chemically reactive versions, and the conjugates prepared therefrom.

SUMMARY OF THE INVENTION

Embodiments of the present invention provide cyanine quencher compounds, which are non-fluorescent or essentially non-fluorescent, that are useful in the context of a luminescent donor-quencher energy transfer pair or a donor-quencher-acceptor composition. These quencher compounds find particular application in biomolecule assays including protein detection, nucleic acid hybridization assays and nucleic acid synthesis wherein fluorescence energy transfer is employed for detection purposes. The present cyanine quencher compounds function as an acceptor in an energy transfer pair wherein the luminescent donor molecule is quenched providing molecules that can be used in a number of assays well known in the art. However, we have found that a particularly useful application is when the quencher compound is part of a composition that comprises a luminescent donor molecule and a luminescent acceptor molecule wherein the quencher compound and the luminescent acceptor compound both accept fluorescent from the donor molecule.

In an exemplary embodiment, the present compounds are according to the formula:

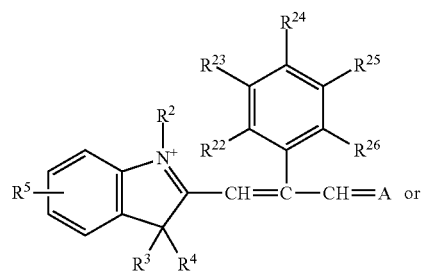

-continued

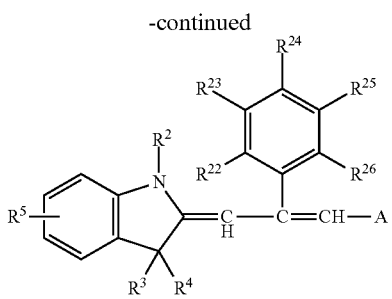

wherein $R^2$ is alkyl, substituted, alkyl, alkoxy, substituted alkoxy, sulfoalkyl, substituted sulfoalkyl, aminoalkyl, substituted aminoalkyl, reactive group, substituted reactive group, carrier molecule, substituted carrier molecule, solid support or substituted solid support;

$R^3$ is alkyl, substituted alkyl, sulfoalkyl, reactive group, substituted reactive group, carrier molecule, substituted carrier molecule, solid support or substituted solid support;

$R^4$ is alkyl, substituted alkyl, sulfoalkyl, reactive group, substituted reactive group, carrier molecule, substituted carrier molecule, solid support or substituted solid support; or $R^3$ and $R^4$ taken together form a 5- or 6-membered saturated ring or a substituted 5- or 6-membered saturated ring;

each $R^5$ is independently hydrogen, alkyl, substituted alkyl, alkoxy, substituted alkoxy, fused benzene, substituted fused benzene, trifluoromethyl, sulfoalkyl, substituted sulfoalkyl, aminoalkyl, substituted aminoalkyl, halogen, reactive group, substituted reactive group, carrier molecule, substituted carrier molecule, solid support or substituted solid support;

$R^{22}$, $R^{23}$, $R^{24}$, $R^{25}$ and $R^{26}$ are independently hydrogen, alkyl, substituted alkyl, alkoxy, substituted alkoxy, amino, substituted amino, aminoalkyl, substituted aminoalkyl, hydroxyl, halogen, thioether, carbonyl, substituted carbonyl, sulfo, substituted sulfo, sulfoalkyl, reactive group, substituted reactive group, carrier molecule, substituted carrier molecule, solid support or substituted solid support; and A is substituted pyridinium, unsubstituted pyridinium, substituted quinolinium, unsubstituted quinolinium, substituted benzazolium, unsubstituted benzazolium, substituted indolinium, or substituted indolinium.

In one aspect, the present compounds have the following formula:

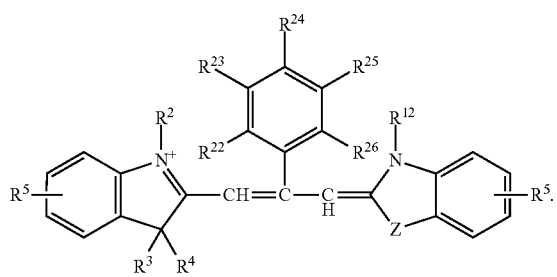

In other embodiments, the present compounds form compositions that comprise a luminescent donor molecule, a luminescent acceptor molecule and a carrier molecule. These compositions may be used to detect the presence or absence of an analyte in a sample. The present quencher compounds can be used in a wide range of assays that employ a luminescent donor-quencher pair. When the composition further comprises a luminescent acceptor, such compositions find use is accepting the residual fluorescence from the donor, which is particularly useful in flow cytometry application when the donor molecule is a fluorescent protein such as phycoerythrin.

Further embodiments include kits for the detection of an analyte and kits that find use in labeling a carrier molecule with a present quencher compounds.

DETAILED DESCRIPTION OF THE INVENTION

Definitions

Figure 1:
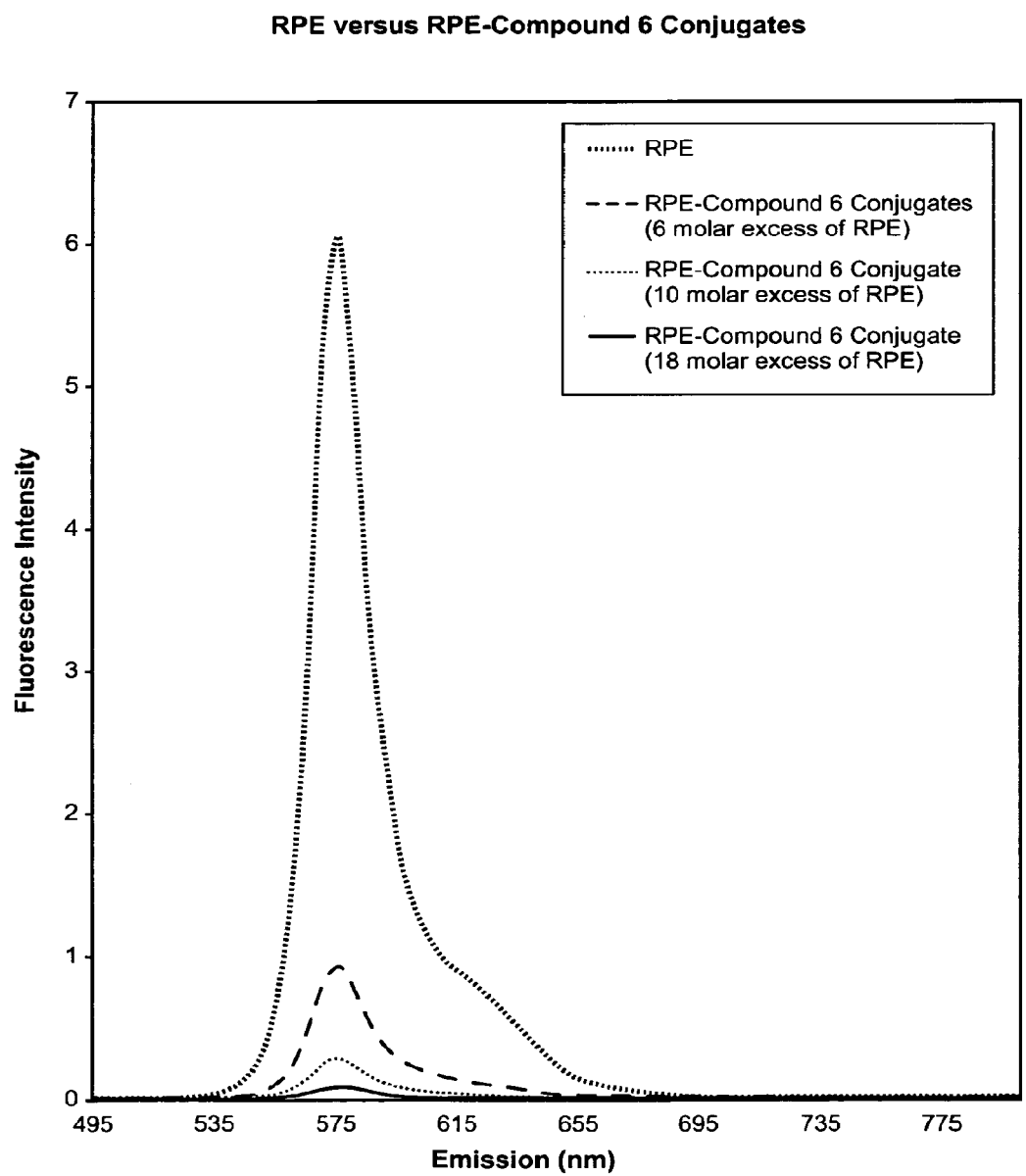
FIG. 1: Shows the emission of R-PE and the quenching of the signal when compound 6 is conjugated to the R-PE demonstrating the ability of compound 6 to quench the emission of R-PE when excited at 488 nm. Compound 6 was conjugated to R-PE at three different molar excesses of Compound 6, 6 molar excess, 10 molar excess and 18 molar excess; these conjugates show a quenching efficiency at 575 nm of 84.4%, 95.2%, and 98.6% respectively, compared to unmodified R-PE excited at the same wavelength. See, Example 8

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a non-fluorescent compound"

includes a plurality of compounds and reference to "a luminescent acceptor molecule" includes a plurality of molecules and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —$CH_2O$— is intended to also recite —$OCH_2$—. The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally quaternized. The heteroatom(s) O, N, P, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R' and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or N$^+$RR'R") where R, R' and R" are independently selected from the group consisting of hydrogen, alkyl, substituted alkyl, aryl, substituted aryl, arylalkyl, substituted arylalkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "biotin-binding protein" as used herein refers to any protein that binds selectively to biotin, including without limitation, antibodies to biotin, substituted or unsubstituted avidin, and analogs and derivatives thereof, as well as substituted and unsubstituted derivatives of antibodies, streptavidin, ferritin avidin, nitroavidin, nitrostreptavidin, Neutravidin™ avidin (a de-glycosylated modified avidin having an isoelectric point near neutral) and their dye-, enzyme-, or polymer-modified variants and immobilized forms of the biotin-binding proteins.

The term "carrier molecule" as used herein refers to a compound of the present invention that is covalently bonded to a biological or a non-biological component. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "cyanine dye" as used herein refers to a non-fluorescent compound that comprises 1) a substituted or unsubstituted indolium moiety, 2) a polymethine bridge that is substituted by at least one aromatic, heteroaromatic, cyclic or heterocyclic moiety and 3) a substituted or unsubstituted indolium, benzazolium, pyridinium or quinolinium moiety.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that is inherently fluorescent or demonstrates a change in fluorescence upon binding to a biological compound or metal ion, or metabolism by an enzyme, i.e., fluorogenic. The dyes of the present invention can function as either fluorescence donor molecules or fluorescence acceptor molecules. Numerous fluorophores are known to those skilled in the art and include, but are not limited to, coumarin, acridine, furan, dansyl, cyanine, pyrene, naphthalene, benzofurans, quinolines, quinazolinones, indoles, benzazoles, borapolyazaindacenes, oxazine and xanthenes, with the latter including fluoresceins, rhodamines, rosamine and rhodols as well as other fluorophores described in RICHARD P. HAUGLAND, MOLECULAR PROBES HANDBOOK OF FLUORESCENT PROBES AND RESEARCH CHEMICALS ($9^{th}$ edition, including the CD-ROM, September 2002). The fluorophore moiety may be substituted by substituents that enhance solubility, live cell permeability and alter spectra absorption and emission.

The term "energy transfer" as used herein refers to the process by which the excited state energy of an excited group, e.g. fluorescent reporter dye, is conveyed through space or through bonds to another group, e.g. a quencher moiety or fluorescer, which may attenuate (quench) or otherwise dissipate or transfer the energy to another reporter group or emit the energy at a longer wavelength. Energy transfer typically occurs through fluorescence resonance energy transfer (FRET).

The term "energy transfer pair" as used herein refers to any two moieties that participate in excited energy transfer. Typically, one of the moieties acts as a fluorescent reporter, i.e. donor, and the other acts as an acceptor, which may be a quenching compound or a compound that accepts and re-emits energy in the form of a fluorescent signal ("Fluorescence resonance energy transfer." Selvin P. (1995) Methods Enzymol 246:300-334; dos Remedios C. G. (1995) J. Struct. Biol. 115:175-185; "Resonance energy transfer: methods and applications." Wu P. and Brand L. (1994) Anal Biochem 218:1-13). FRET is a distance-dependent interaction between two moieties in which excitation energy, i.e. light, is transferred from a donor to an acceptor without emission of a photon. The acceptor may be fluorescent and emit the transferred energy at a longer lower energy wavelength, or it may be non-fluorescent and serve to diminish the detectable fluorescence of the reporter molecule (quenching). FRET may be either an intermolecular or intramolecular event, and is dependent on the inverse sixth power of the separation of the donor and acceptor, making it useful over distances comparable with the dimensions of biological macromolecules. Thus, the spectral properties of the energy transfer pair as a whole change in some measurable way if the distance between the moieties is altered by some critical amount. Self-quenching probes incorporating fluorescent donor-non-fluorescent acceptor combinations have been developed primarily for detection of proteolysis (Matayoshi, (1990) Science 247:954-958) and nucleic acid hybridization ("Detection of Energy Transfer and Fluorescence Quenching" Morrison, L., in Nonisotopic DNA Probe Techniques, L. Kricka, Ed., Academic Press, San Diego, (1992) pp. 311-352; Tyagi S. (1998) Nat. Biotechnol. 16:49-53; Tyagi S. (1996) Nat. Biotechnol 14:303-308). Other biological assays using FRET are described in the following references: Holskin, B. P.; Bukhtiyarova, M.; Dunn, B. M.; Baur, P.; Dechastonay, J.; Pennington, M. W. Anal Biochem 1995, 227, 148-155; Beekman, B.; Drijfhout, J. W.; Bloemhoff, W.; Ronday, H. K.; Tak, P. P.; to Koppele, J. M. FEBS Lett 1996, 390, 221-225; Pennington, M. W.; Thornberry, N. A. Peptide Research 1994, 7, 72-76; Wang, Q. M.; Johnson, R. B.; Cohen, J. D.; Voy, G. T.; Richardson, J. M.; Jungheim, L. N. Antivir Chem Chemother 1997, 8, 303-310; Gulnik, S. V.; Suvorov, L. I.; Majer, P.; Collins, J.; Kane, B. P.; Johnson, D. G.; Erickson, J. W. FEBS Lett 1997, 413, 379-384; Beekman, B.; van El, B.; Drijfhout, J. W.; Ronday, H. K.; TeKoppele, J. M. FEBS Lett 1997, 418, 305-309; and Beebe, K. D.; Pei, D. Anal Biochem 1998, 263, 51-56. In most applications, the donor and acceptor dyes are different, in which case FRET can be detected by the appearance of sensitized fluorescence of the acceptor or by quenching of donor fluorescence.

The term "kit" as used refers to a packaged set of related components, typically one or more compounds or compositions.

The term "linker" as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. The linker can be used to attach the compound to another component of a conjugate, such as a targeting moiety (e.g., antibody, ligand, non-covalent protein-binding group, etc.), an analyte, a biomolecule, a drug and the like.

The term "cleavable linker" as used herein is a linker that has one or more chemical bonds that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. An exemplary cleavable group, an ester, is cleavable group that may be cleaved by a reagent, e.g., sodium hydroxide, resulting in a carboxylate-containing fragment and a hydroxyl-containing product. Many cleavable groups are known in the art. See, for example, Jung et al., *Biochem. Biophys. Acta*, 761: 152-162 (1983); Joshi et al., *J. Biol. Chem.*, 265: 1 451 8-1 4525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

The terms "protein" and "polypeptide" are used herein in a generic sense to include polymers of amino acid residues of any length. The term "peptide" as used herein refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in *Chemistry and Biochemistry of Amino Acids, Peptides and Proteins*, B. Weinstein, eds., Marcel Dekker, New York, p. 267 (1983).

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but are not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "reporter molecule" as used herein refers to any luminescent molecule that is capable of functioning as a member of an energy transfer pair. Typically, reporter molecules include fluorescent proteins, fluorescent dyes and chemiluminescent compounds that are capable of producing a detectable signal upon appropriate activation.

The term "sample" as used herein refers to any material that may contain a target ligand. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The term "Stokes shift" as used herein refers to the difference in wavelength between absorbed and emitted energy. Specifically, the Stokes shift is the difference (usually in frequency units) between the spectral positions and the band maxima (or band origin) of the absorption and luminescence arising from the same electronic transitions.

Cyanine Compounds

In general, for ease of understanding the present invention, the cyanine compounds and corresponding substituents will first be described in detail, followed by the many and varied methods in which the compounds find uses, which is followed by exemplified methods of use and synthesis of certain novel compounds that are particularly advantageous for use with the methods of the present invention.

The compounds of the present invention are cyanine compounds that are essentially non-fluorescent and have an absorption maximum at about 580-650 nm and an extinction coefficient of about 30,000 $cm^{-1}M^{-1}$ or greater. These compounds are substituted on the methane bridge by an aromatic, heteroaromatic, cyclic or heterocyclic moiety. The presence of this ring substituent along with a terminal indolinium moiety results in non-fluorescent compounds that quench the signal from a luminescent donor molecule that emits in the range in which the present compounds absorb. The present cyanine compounds find utility as quenchers of a luminescent donor molecule wherein the luminescent donor molecule and present compounds function as an energy transfer pair. Unexpectedly, they also find utility for improving the overall use of tandem conjugates wherein the present compounds reduce the residual unquenched donor fluorescence that is normally present with tandem conjugates. This improvement is important because there is a reduced residual fluorescence of the phycobiliprotein donor (fluorescent proteins), resulting in a decreased necessity to compensate for this residual fluorescence in experimental protocols wherein the primary fluorescent signal being observed is from the transferred energy emitted by the acceptor molecule.

In an exemplary embodiment, the cyanine compounds of the present invention comprise an indolium moiety that is bonded to another terminal aromatic subunit by a polymethine bridge wherein the polymethine bridge is substituted by an aromatic substituent. Without wishing to be bound by a theory it appears that the addition of the aromatic substituent has not effect, or minimal effect, on the absorption spectra while having a significant effect on the emission spectra of the compound. This observed effect may be the result of a disruption in the conjugation between the indolium moiety and the terminal aromatic subunit, or the addition of the aromatic substituent may provide alternative depopulation pathways.

There is no intended limitation of the methine bridge ring substituent, which is an aromatic, heteroaromatic, cyclic or heterocyclic moiety. The ring moiety contains 3-20 non-hydrogen atoms selected from the group consisting of C, N, O, S, and P. This moiety in its self may confer rigidity to the cyanine compound wherein conjugation is disrupted or the bulkiness of the substituent alters the conjugation with making the methine bridge ridge. Alternatively the conjugation is not at all, or only partially, disrupted wherein the absorption spectra is not significantly altered but the emission spectra is significantly altered. These methine ring substituents have novel properties in forming non-fluorescent cyanine compounds. The methine bridge ring substituent is an aromatic, heteroaromatic, cyclic or heterocyclic moiety, which includes, but is not limited to, phenyl, adamentane, benzene, pyrimidine, piperazine, piperidine, cyclohexane, cyclopentane, dioxane, tetrahydropyran, tetrahydrofuran, pyrole, thiophene, furna, oxazole, pyridine, thiazole, cyclen and pyrolidine In an exemplary embodiment the present cyanine compounds are represented by the following formula:

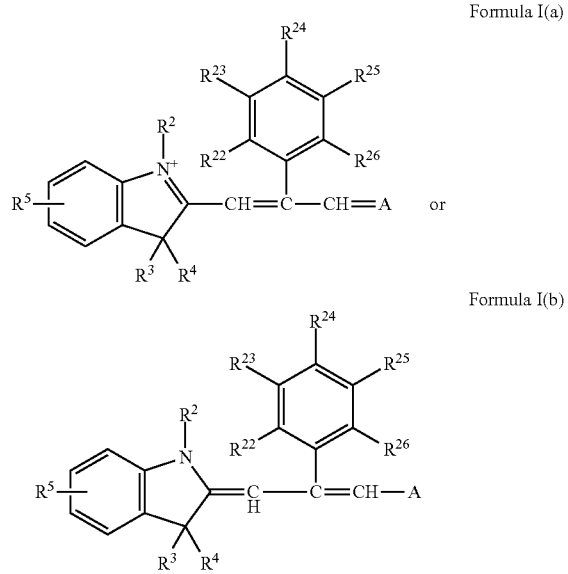

The nitrogen substituent $R^2$ is alkyl, substituted alkyl, alkoxy, substituted alkoxy, sulfoalkyl, substituted sulfoalkyl, aminoalkyl or substituted aminoalkyl, reactive group, substituted reactive group, carrier molecule, substituted carrier molecule, solid support or substituted solid support. Alternatively, $R^2$ is a substituted or unsubstituted aromatic, heteroaromatic, cyclic or heterocyclic moiety. Each alkyl portion of $R^2$ is optionally further substituted by substituents selected from the group consisting of carboxy, sulfo, amino, and hydroxy.

In one aspect $R^2$ is an alkyl, typically a methyl. Alternatively, $R^2$ is a reactive group, carrier molecule or solid support. In one aspect $R^2$ is a reactive group, in another aspect $R^2$ is a carrier molecule.

$R^3$ and $R^4$ are independently alkyl, substituted alkyl, sulfoalkyl, substituted sulfoalkyl, reactive group, substituted reactive group, carrier molecule, substituted carrier molecule, solid support or substituted solid support. Alternatively, $R^3$ and $R^4$ taken together form a 5- or 6-membered saturated ring, which may be substituted by a reactive group, carrier molecule, solid support, alkyl, alkoxy, sulfoalkyl or amino.

Each alkyl portion of $R^3$ and $R^4$ optionally incorporates up to six hetero atoms, selected from the group consisting of N, O and S, and is independently and optionally substituted one or more times by substituents selected from the group consisting of F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, and $C_3$-$C_{18}$ trialkylammonium.

The carbon ring substitutent, $R^5$ is independently hydrogen, alkyl, substituted alkyl, alkoxy, substituted alkoxy, halogen, fused benzene, substituted fused benzene, trifluoromethyl, sulfo (—$SO_3^-$), substituted sulfo (—($SO_2$)—$R^{27}$, —(SO)—$R^{27}$), sulfoalkyl, substituted sulfoalkyl, aminoalkyl, substituted aminoalkyl, halogen, reactive group, substituted reactive group, carrier molecule, substituted carrier molecule, solid support or substituted solid support. $R^{27}$ is hydrogen, amine, substituted amine, alkyl or substituted alkyl.

The indolium moiety may contain more than one $R^5$, (1-4), which may be the same or different. Each alkyl portion of $R^5$ is optionally further substituted by substituents selected from the group consisting of carboxy, sulfo, amino, and hydroxy; or any two adjacent substituents form a fused benzo ring that is optionally substituted one or more times by substituents selected from the group consisting of reactive group, carrier molecule, solid support, amino, sulfo, trifluoromethyl, halogen, $C_1$-$C_6$ alkyl, $C_1$-$C_6$ alkoxy, $C_1$-$C_6$ alkylamino, and $C_2$-$C_{12}$ dialkylamino. Each of these alkyl portions are optionally further substituted by substituents selected from the group consisting of carboxy, sulfo, amino, and hydroxy.

$R^5$ is typically hydrogen, but substituents other than hydrogen may be used. In one aspect of the invention the carbon ring substituents are hydrogen. In another aspect, at least one of the carbon ring substituents is a sulfo group (—$SO_3^-$) or substituted sulfo group, wherein the sulfo group increases the solubility of the present compounds.

In one embodiment, the aromatic moiety substituent on the trimethine bridge is a phenyl ring. The phenyl substituents ($R^{22}$, $R^{23}$, $R^{24}$, $R^{25}$ and $R^{26}$) are hydrogen, alkyl, substituted alkyl, alkoxy, substituted alkoxy, amino, substituted amino, aminoalkyl, substituted aminoalkyl, hydroxyl, halogen, thioether, carbonyl (—C=O—), substituted carbonyl (—(C=O)—NR'R", —(C=O)—O—$R^{27}$, —(C=O)—$R^{27}$), sulfo (—$SO_3$), substituted sulfo (—($SO_2$)—$R^{27}$, —(SO)—$R^{27}$), reactive group, substituted reactive group, carrier molecule, substituted carrier molecule, solid support or substituted solid support. $R^{27}$ is hydrogen, amine, substituted amine, alkyl or substituted alkyl and R' and R" are independently hydrogen, alkyl or aminoalkyl.

Alternatively, any two adjacent $R^{22}$, $R^{23}$, $R^{24}$, $R^{25}$ and $R^{26}$ substituents combine to form a fused ring that is optionally further substituted. In this instance, $R^{22}$ in combination with $R^{23}$; $R^{23}$ in combination with $R^{24}$; $R^{24}$ in combination with $R^{25}$; or $R^{25}$ in combination with $R^{26}$; together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl. Adjacent $R^{22}$, $R^{23}$, $R^{24}$, $R^{25}$ and $R^{26}$ may combine to form one fused ring or they may combine to form multiple fused rings.

In one aspect of the invention each $R^{22}$, $R^{23}$, $R^{24}$, $R^{25}$ and $R^{26}$ is hydrogen. In another aspect, at least one of $R^{22}$, $R^{23}$, $R^{24}$, $R^{25}$ and $R^{26}$ is substituted by an alkyl group or —(C═O)—O—$R^{27}$ wherein $R^{27}$ is —CH$_3$. Preferably $R^{24}$ is substituted by —(C═O)—O—$R^{27}$.

The A moiety of the present invention is selected in such a way as to form either symmetrical or unsymmetrical cyanine compounds. The A moiety is not intended to be limiting but instead can be any cyanine subunit known to one skilled in the art, including those subunits disclosed in U.S. Pat. Nos. 4,957,870; 4,883,867; 5,436,134; 5,658,751, 5,534,416; 5,863,753; 5,853,969; 6,225,050; 6,048,982; 5,627,027; 5,569,766; 5,569,587; 5,268,486; 6,114,350; 6,197,956; 6,204,389; 6,224,644 and 5,486,616. In an exemplary embodiment A is a substituted pyridinium, unsubstituted pyridinium, substituted quinolinium, unsubstituted quinolinium, substituted benzazolium, unsubstituted benzazolium, substituted indolinium, substituted indolinium.

In one aspect of the invention A is:

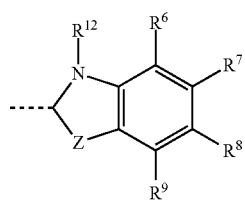

Formula (II)

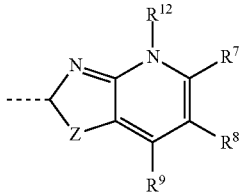

Formula (III)

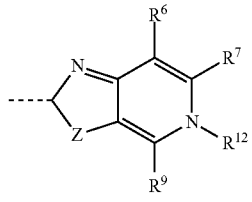

Formula IV

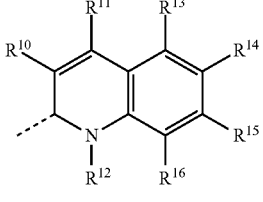

Formula V

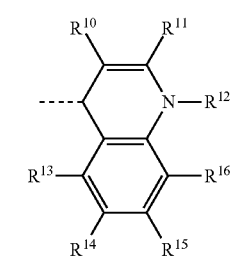

Formula VI

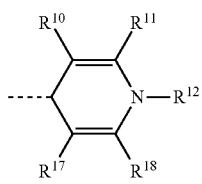

Formula VII

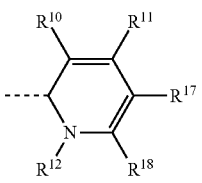

Formula VIII

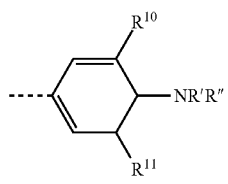

Formula IX

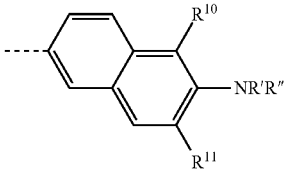

Formula X

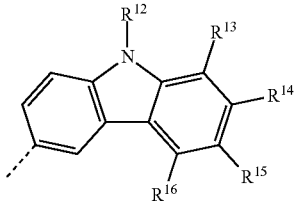

Formula XI

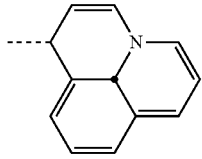

Formula XII

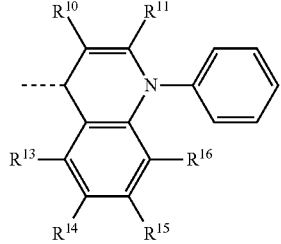

Formula XIII wherein the dashed line represents the point of attachment to the polymethine bridge and is a double or single bond to a carbon of a methine group, depending on the compound (Formula I(a) or Formula I(b)) and the distribution of the positive charge on the quaternized nitrogen.

Z is a heteroatom or carbon atom. Typically, Z is selected from the group consisting of S, O, $NR^{12}$ and $CR^3R^4$ (defined above). The nitrogen substituent, $R^{12}$ is alkyl, substituted, alkyl, alkoxy, substituted alkoxy, sulfoalkyl, substituted sulfoalkyl, aminoalkyl or substituted aminoalkyl, reactive group, substituted reactive group, carrier molecule, substituted carrier molecule, solid support or substituted solid support. Alternatively, $R^{12}$ is a substituted or unsubstituted aromatic, heteroaromatic, cyclic or heterocyclic moiety (Formula XIII). Each alkyl portion of $R^{12}$ is optionally further substituted by substituents selected from the group consisting of carboxy, sulfo, amino, aminoalkyl and hydroxy.

In one aspect $R^{12}$ is an alkyl, typically a methyl. Alternatively, $R^{12}$ is a reactive group, carrier molecule or solid support. In one aspect $R^{12}$ is a reactive group, in another aspect $R^{12}$ is a carrier molecule. In an exemplary embodiment, at least one of $R^2$ or $R^{12}$ is a reactive group, solid support or carrier molecule wherein the other is alkyl, typically methyl. Typically the reactive group is amine- or thiol-reactive to facilitate conjugation with a biological carrier molecule.

In another aspect of the invention, $R^3$ and $R^4$ are independently alkyl groups, sulfoalkyl, reactive group, solid support or carrier molecule. Typically the alkyl group is a methyl group, $—CH_3$. In a further aspect of the invention at least one of $R^3$ and $R^4$ is a reactive group, wherein the remaining substituents are alkyl or sulfoalkyl groups. Typically the reactive group is amine- or thiol-reactive to facilitate conjugation with a biological carrier molecule.

In another aspect, at least one of $R^2$, $R^{12}$, $R^3$ and $R^4$ is a reactive group, solid support or carrier molecule. Typically the remaining $R^2$, $R^{12}$, $R^3$ and $R^4$ are methyl or sulfoalkyl.

The carbon ring substituents $R^6$, $R^7$, $R^8$, $R^9$, $R^{10}$, $R^{11}$, $R^{13}$, $R^{14}$, $R^{15}$, $R^{16}$, $R^{17}$ and $R^{18}$ are independently hydrogen, alkyl, substituted alkyl, alkoxy, substituted alkoxy, sulfo, substituted sulfo, sulfoalkyl, substituted sulfoalkyl, amino, substituted amino, aminoalkyl, substituted aminoalkyl, trifluoromethyl, halogen, reactive group, substituted reactive group, carrier molecule, substituted carrier molecule, solid support or substituted solid support. Each alkyl portion of the carbon ring substituents are optionally further substituted by substituents selected from the group consisting of carboxy, sulfo, amino, and hydroxyl.

The nitrogen substituents R' and R" are hydrogen, alkyl or aminoalkyl.

Alternatively, any two adjacent substituents, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, R' and R" form a fused benzo ring that is optionally substituted one or more times by substituents selected from the group consisting of reactive group, carrier molecule, solid support, amino, sulfo, trifluoromethyl, halogen, alkyl, alkoxy, alkylamino, and dialkylamino. Each of these alkyl portions are optionally further substituted by substituents selected from the group consisting of carboxy, sulfo, amino, and hydroxy.

In one aspect, $R^6$ in combination with $R^7$; $R^7$ in combination with $R^8$; $R^8$ in combination with R9; $R^{10}$ in combination with $R^{11}$; $R^{11}$ in combination with $R^{13}$; $R^{13}$ in combination with $R^{14}$; $R^{14}$ in combination with $R^{15}$; $R^{15}$ in combination with $R^{16}$; $R^{11}$ in combination with $R^{17}$; $R^{17}$ in combination with $R^{18}$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl.

In another aspect, $R^{12}$ in combination with $R^6$; $R^{12}$ in combination with $R^7$; $R^{12}$ in combination with $R^9$; $R^{12}$ in combination with $R^{16}$; $R^{12}$ in combination with $R^{18}$, $R^{12}$ in combination with $R^{11}$; $R^{10}$ in combination with R'; $R^{11}$ in combination with R"; or R' in combination with R" together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl.

In one aspect of the invention the carbon ring substituents are hydrogen. In another aspect, at least one of the carbon ring substituents is a sulfo group, $—SO_3^-$ or sulfoalkyl, wherein the sulfo group increases the solubility of the present compounds. Typically, when at least one of the carbon ring substituents is a sulfo group, it is present at $R^8$.

In an exemplary embodiment A moiety is:

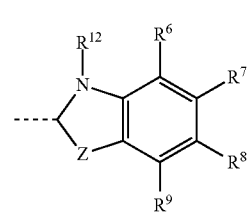

Formula (II)

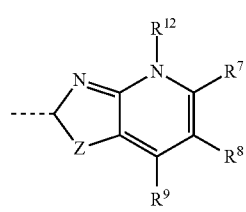

Formula (III)

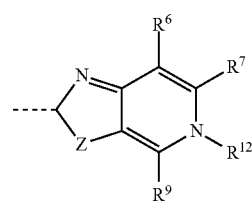

Formula IV

In another exemplary embodiment, A is:

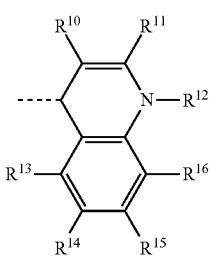

Formula VI

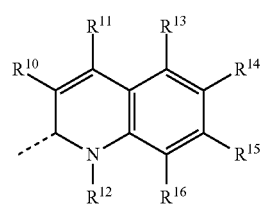

Formula V

Thus, a preferred compound of the present invention has the following formula:

Formula (XIV)

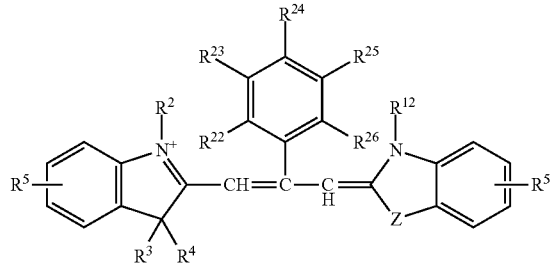

Wherein the A moiety is formula (II) and Z is O or $CR^3R^4$.

The phenyl substituents are as described above. Typically, $R^{22}$, $R^{23}$, $R^{24}$, $R^{25}$ and $R^{26}$ are hydrogen or at least one phenyl substitutent is —(C=O)—O—$R^{27}$ wherein $R^{27}$ is an alkyl group. Preferably all phenyl substituents are hydrogen or $R^{24}$ is —(C=O)—O—$CH_3$ and the remaining phenyl substituents are hydrogen.

$R^5$ is as described above. Typically the benzo substituents are hydrogen or a solubilizing group such as —$SO_3^-$ or sulfoalkyl.

$R^3$ and $R^4$ areas described above. Typically, these substituents are a lower alkyl group, sulfoalkyl, reactive group, carrier molecule or solid support. More than one of the substituents may be reactive group, solid support or carrier molecule wherein the remaining groups are typically methyl groups, —$CH_3$. In one aspect of the invention exactly one of $R^3$ and $R^4$ is reactive group, solid support or carrier molecule and the remaining substituents are methyl groups. Typically, the reactive group is a group that reacts with amines, thiols or other nulceophiles/electrophiles present on proteins such as carboxylic acids or activated esters of carboxylic acid. The carrier molecule is typically a streptavidin or avidin, a biotin, an antibody or fragment thereof, a protein A, an oligonucleotide or a nucleotide.

$R^2$ and $R^{12}$ are as described above. Typically, $R^2$ and $R^{12}$ are independently an alkyl group, sulfoalkyl, reactive group, solid support or carrier molecule. In one aspect of the invention, $R^2$ is methyl. Alternatively, at least one of one of $R^2$ and $R^{12}$ are a reactive group, solid support or carrier molecule and the remaining $R^2$ and $R^{12}$ is methyl or sulfoalkyl. In another aspect, both $R^2$ and $R^{12}$ are a reactive group, solid support or carrier molecule.

Preferred compounds that are represented by formula (XII) include compounds 2-6. (See, Examples 2-6).

In another aspect of the invention, preferred compounds are represented by the following formula:

Formula (XV)

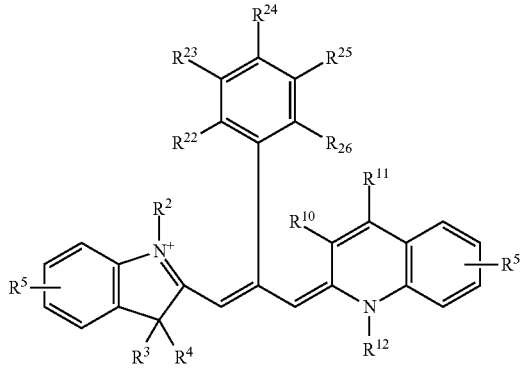

The phenyl substituents are as described above. Typically, $R^{22}$, $R^{23}$, $R^{24}$, $R^{25}$ and $R^{26}$ are hydrogen or at least one phenyl substituent is —(C=O)—O—$R^{27}$ wherein $R^{27}$ is an alkyl group. Preferably, all phenyl substituents are hydrogen or $R^{24}$ is —(C=O)—O—$CH_3$ and the remaining phenyl substituents are hydrogen.

The carbon ring substituents, herein represented as $R^5$ ($R^{13}$-$R^{16}$) are as described above. Preferably the substituents are hydrogen or a solubilizing group such as a sulfo group or sulfoalkyl. Alternatively, the carbon ring substituents are a reactive group, solid support or carrier molecule.

$R^3$ and $R^4$ are as described above. Preferably, these substituents are a lower alkyl group, sulfoalkyl, reactive group, solid support or carrier molecule. In one aspect of the invention, both $R^3$ and $R^4$ are methyl. In another aspect $R^3$ is a reactive group, solid support or carrier molecule and $R^4$ is methyl.

$R^2$ and $R^{12}$ are as described above. Typically, $R^2$ and $R^{12}$ are independently a lower alkyl, sulfoalkyl, reactive group, solid support or carrier molecule. In one aspect of the invention, $R^2$ and $R^{12}$ are methyl. In another aspect, at least one of $R^2$ and $R^{12}$ is a reactive group, solid support or carrier molecule and the other is a methyl or sulfoalkyl.

Compound 7 is a preferred compound that is represented by Formula (VIII). See, Example 7.

In another aspect of the invention, preferred compounds are represented by the following formula:

Formula (XVI)

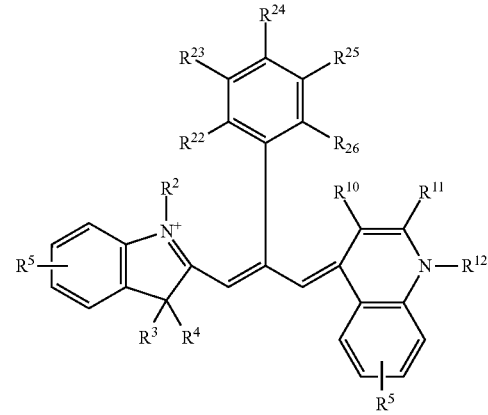

Synthesis

A useful synthetic route to the cyanine compounds of the present invention can be described in two parts: 1) the indolium moiety containing the aromatic methine substituent and 2) the addition of the A moiety. Typically, each component is selected so as to incorporate the appropriate chemical substituents, or functional groups that can be converted to the appropriate substituents. The chemistry that is required to prepare and combine these precursors so as to yield any of the subject derivatives is generally well understood by one skilled in the art. Although there are many possible variations that may yield an equivalent result, we provide herein some useful general methods for their synthesis and incorporation of chemical modifications.

Synthesis of the non-fluorescent carbocyanine compounds of the invention, with an aromatic substituent on the trimethine bridge, depends on initial preparation of certain key intermediates, the indolium moiety containing the aromatic methine substituent. The intermediates have the following general structure (for simplicity, all but a few of the possible substituents are shown as hydrogen):

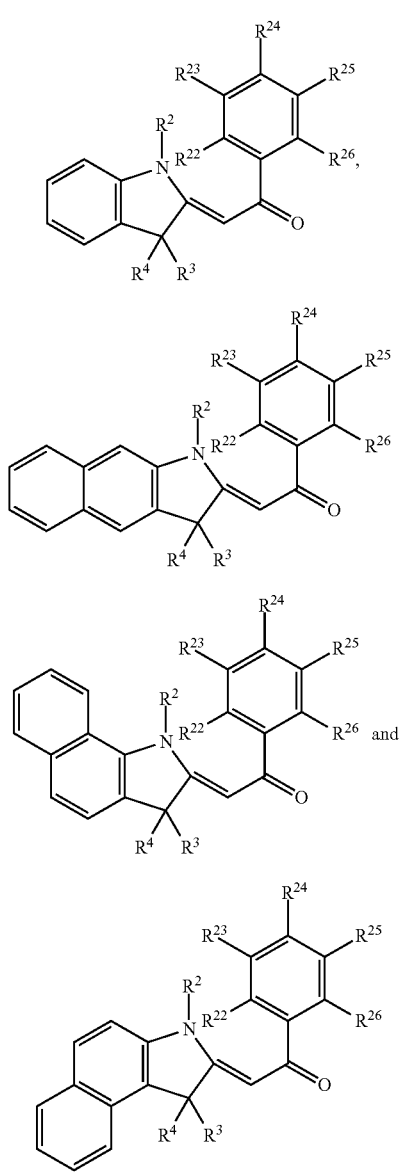

Formula (XVII)

Formula (XVIII)

Formula (XIX)

Formula (XX)

The indolenine moiety is first synthesized by a Fischer indole synthesis. In this reaction, an appropriately substituted aryl hydrazine, is reacted with an appropriately substituted methyl ketone to yield a 2-methylindolenine, which is then quaternized with an appropriate alkylating reagent to generate the indolium or indoleninium derivative. The alkylating reagent is typically an alkyl halide such as ethyl iodide, an alkylsulfonate such as methyl p-toluenesulfonate or a cyclic sulfonate such as propanesultone or butanesultone. Reactive groups can be introduced at this site by alkylation with a derivative that is, or can be converted to, a reactive group. In particular, omega-haloalkanoic acids can be used to introduce alkanoic acids, which can be converted to amine-reactive active esters. The indolium or indoleninium moiety is subsequently reacted with an aromatic acid chloride to generate the desired benzoketone key intermediate. The benzoketone can be activated by phosphorous oxychloride to a chloro derivative that can be condensed with the A moiety resulting in the present compounds of the invention.

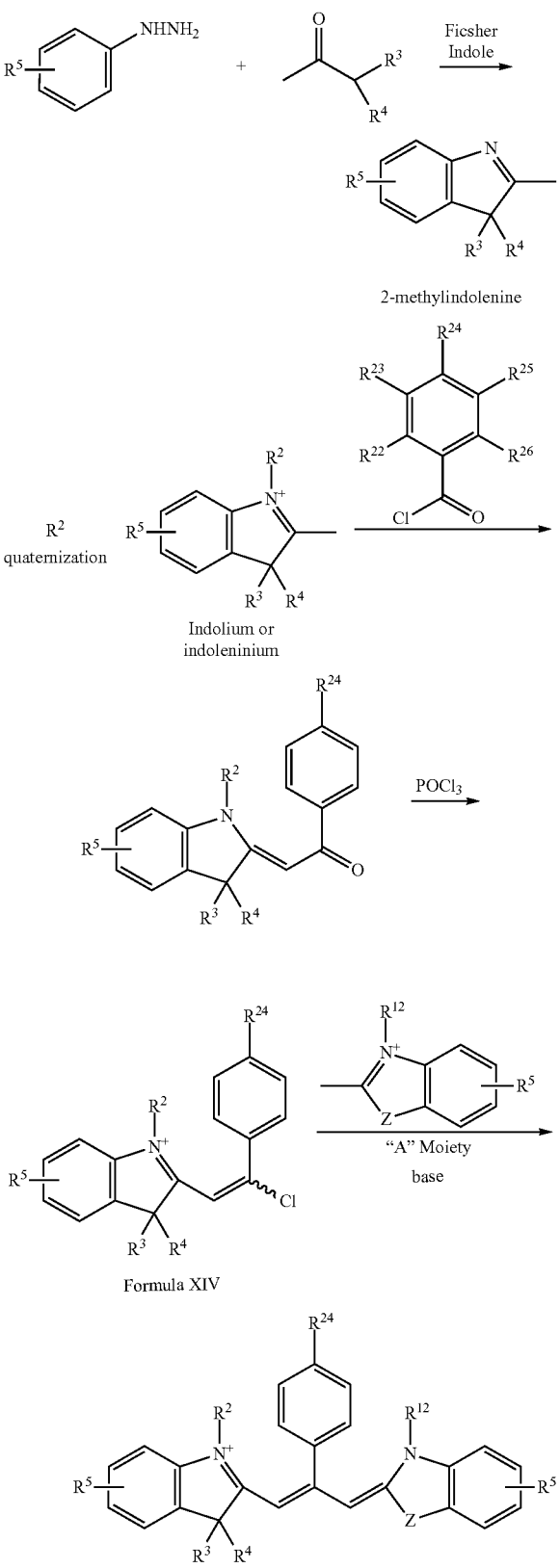

Thus, in one aspect of the invention, the synthetic intermediate is a compound of the formula:

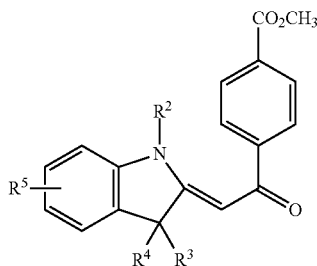

Formula XXI or its activated form, wherein $R^3$ and $R^4$ are an alkyl or a carboxyalkyl; $R^2$ is a reactive group, solid support, carrier molecule, alkyl, alkyl substituted by sulfo or carboxyalkyl; $R^5$ is independently hydrogen, amino, sulfo, trifluoromethyl, or halogen; or $C_1$-$C_6$ alkyl, $C_1$-$C_6$ alkoxy, $C_1$-$C_6$ alkylamino, $C_2$-$C_{12}$ dialkylamino, each of which is optionally further substituted by carboxy, sulfo, amino, or hydroxy; or any two adjacent substituents form a fused benzo ring that is optionally substituted one or more times by amino, sulfo, trifluoromethyl, or halogen; or by $C_1$-$C_6$ alkyl, $C_1$-$C_6$ alkoxy, $C_1$-$C_6$ alkylamino, $C_2$-$C_{12}$ dialkylamino, each of which is optionally further substituted by carboxy, sulfo, amino, or hydroxy. In a preferred embodiment, $R^3$ is sulfoalkyl, $C_5$-$C_6$ carboxyalkyl; and $R^4$ is methyl or $R^3$ and $R^4$ are both methyl; $R^2$ is methyl, carboxyalkyl, sulfopropyl or $C_5$-$C_6$ carboxyalkyl; and $R^5$ is independently hydrogen or sulfo.

The A moiety intermediate is as described above, and are well known in the art (for example, U.S. Pat. No. 5,436,134). The A moiety is optionally fused to additional rings, resulting in dyes that absorb at longer wavelengths (for example, see U.S. Pat. No. 6,027,709). The A moiety is subsequently condensed with an indolium moiety to generate the present nonfluorescent carbocyanine compounds.

Reactive Groups, Carrier Molecules and Solid Supports

The present compounds, in certain embodiments, are chemically reactive wherein the compounds comprise a reactive group. In a further embodiment, the compounds comprise a carrier molecule or solid support. These substituents, reactive groups, carrier molecules, and solid supports, comprise a linker that is used to covalently attach the substituents to any of the moieties of the present cyanine compounds. The solid support, carrier molecule or reactive group may be directly attached (where linker is a single bond) to the moieties or attached through a series of stable bonds, as disclosed above.

Any combination of linkers may be used to attach the carrier molecule, solid support or reactive group and the present compounds together. The linker may also be substituted to alter the physical properties of the reporter moiety or chelating moiety, such as spectral properties of the dye.

An important feature of the linker is to provide an adequate space between the carrier molecule, reactive group or solid support and the present cyanine compound so as to prevent steric hindrance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support. Thus, in another aspect of the present invention the compounds comprise the chelating moiety, linker, reporter moiety, a reactive group moiety and optionally a carrier molecule and/or a solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{22}$, $R^{23}$, $R^{24}$, $R^{25}$, and $R^{26}$ are a reactive group or are attached to a reactive group. Preferably, at least one of $R^2$, $R^3$, $R^4$, $R^{12}$, $R^{22}$, $R^{23}$, $R^{24}$, $R^{25}$, and $R^{26}$ is a reactive group or is attached to a reactive group, wherein at least one of $R^2$, $R^3$, $R^4$, or $R^{12}$ is a reactive group or is attached to a reactive group. Alternatively, if the present compound comprises a carrier molecule or solid support a reactive group may be covalently attached independently to those substituents, allowing for further conjugation to a carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine-containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

The pro-reactive groups are synthesized during the formation of the monomer moieties and carrier molecule and solid support containing compounds to provide chemically reactive nucleic acid reporter compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and U.S. Pat. No. 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

In another exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In exemplary embodiment, at least one member selected from $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{22}$, $R^{23}$, $R^{24}$, $R^{25}$, and $R^{26}$ are a carrier molecule or are attached to a carrier molecule. Preferably, at least one of $R^2$, $R^3$, $R^4$, $R^{12}$, $R^{22}$, $R^{23}$, $R^{24}$, $R^{25}$, and $R^{26}$ is a carrier molecule or is attached to a carrier molecule, wherein at least one of $R^2$, $R^3$, $R^4$, or $R^{12}$ is a carrier molecule or is attached to a carrier molecule. Alternatively, if the present compound comprises a carrier molecule or solid support an additional carrier molecule may be covalently attached independently to those substituents, allowing for further conjugation to another carrier molecule or solid support.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCO$alkyl and combinations thereof. Thus, the enzyme substrates can be cleaved by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect nucleic acids. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |

TABLE 2-continued

Representative Specific Binding Pairs

| antigen | antibody |
|---|---|
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization The non-fluorescent carbocyanine compounds of the present invention are employed as energy acceptors that quench a signal from a luminescent donor molecule. Thus, the carbocyanine quencher compounds need to be in sufficiently close proximity to a luminescent donor for energy transfer to be accomplished by any means well known in the art. This can be accomplished when the quencher compound and luminescent donor are attached to different conjugated substances that are brought together, typically through non-covalent binding such as the binding between an antigen and antibody or biotin and biotin-binding protein. Alternatively, the present quencher compounds of the present invention and a luminescent donor are attached to each other, attached to the same conjugated substance or some combination thereof, which may be cleaved to restore fluorescence to the donor molecule. In a particularly useful embodiment, the conjugated substance is not intended to be cleaved because the conjugated substance further comprises a luminescent acceptor molecule wherein the present quencher compound functions to improve the overall energy transfer between the luminescent donor and the luminescent acceptor by absorbing the residual energy from the luminescent donor molecule.

Thus, in another exemplary embodiment, the present compounds are covalently bonded to a luminescent donor molecule and/or a luminescent acceptor molecule, which for the purposes of this invention are considered carrier molecules when covalently bonded to the present compounds. However, it is understood that the below described luminescent acceptor and donor molecules can function as such without being covalently bonded to the present compound. It is an exemplary embodiment that the luminescent acceptor and/or donor molecules are carrier molecules. In one aspect these luminescent molecules are fluorescent dyes, a chemiluminescent compound or a fluorescent protein.

In an exemplary embodiment the present compound is part of a composition wherein the composition comprises:
  a) a luminescent donor molecule; and
  b) a present compound wherein the compound accepts fluorescence from the luminescent donor molecule.

In one aspect this composition is further covalently bonded to another carrier molecule. In this instance, carrier molecules, include, but are not limited to amino acid, a peptide, a protein, a polysaccharide, a nucleoside, a nucleotide, an oligonucleotide, biotin-binding protein, a nucleic acid polymer, a hapten, a psoralen, a drug, a hormone, a lipid, a lipid assembly, a synthetic polymer, a polymeric microparticle, a biological cell or a virus. In a further aspect, the carrier molecule is a streptavidin or avidin, a biotin, an antibody or fragment thereof, a protein A, an oligonucleotide or a nucleotide. In a particular aspect the carrier molecule is an antibody.

These compositions find use in bioassays wherein a gain of a signal, or possibly a loss of a signal, signify the presence or absence of an analyte or event of interest, such as an enzyme or nucleic acid hybridization, respectively.

In another aspect the present compound is part of a composition wherein the composition comprises:
  a. a luminescent donor molecule having a first absorption and emission spectra;
  b. a luminescent acceptor molecule having a second absorption and emission spectra; and,
  c. a present non-fluorescent compound wherein the non-fluorescent compound accepts fluorescence from the luminescent donor molecule.

The luminescent donor molecule and luminescent acceptor molecule are chromophores that are independently selected from the group consisting of a fluorescent dye, a chemiluminescent compound or a fluorescent protein. Typically, when present, the fluorescent protein is a phycobiliprotein. Specifically, phycoerythrin and allophycocyanin are most preferred.

In one aspect, the composition further comprises a carrier molecule wherein the luminescent donor molecule, the luminescent acceptor molecule and the non-fluorescent compound are covalently bonded to the carrier molecule. In this instance, carrier molecules include, but are not limited to amino acid, a peptide, a protein, a polysaccharide, a nucleoside, a nucleotide, an oligonucleotide, biotin-binding protein, a nucleic acid polymer, a hapten, a psoralen, a drug, a hormone, a lipid, a lipid assembly, a synthetic polymer, a polymeric microparticle, a biological cell or a virus. In a further aspect, the carrier molecule is a streptavidin or avidin, a biotin, an antibody or fragment thereof, a protein A, an oligonucleotide or a nucleotide.

These compositions find particular use in a bioassay wherein the luminescent donor is a fluorescent protein and emits fluorescence that is not adequately accepted and absorbed by the luminescent acceptor molecule. This results in an additional fluorescence peak that for multiplexing purposes prevents, the use of the corresponding channel, such as in flow cytomerty. Alternatively, the un-accepted fluorescence can be compensated for, which up until now was accomplished with filters. Herein, we report for the first time, and unexpectedly so, the use a quencher compound to accept the residual fluorescence from the luminescent donor molecule. In one aspect the luminescent donor molecule is fluorescent protein that is phycoerythrin protein.

When the luminescent donor is a protein the quencher compound and luminescent acceptor are typically conjugated to the luminescent protein and then that composition is covalently attached to the member of the specific binding pair resulting in a four part composition. These compositions find utility in accepting the fluorescence from the donor molecule resulting in the reduced need to account for the residual energy generated from the luminescent protein that was not accepted by the luminescent acceptor. Accordingly, a preferred energy transfer composition includes the conjugate R-PE-quencher compound-carbocyanine dye further conjugated to a biotin-binding protein. Particularly preferred is R-PE-Compound 6-Alexa Fluor dye conjugated to streptavidin. See, Examples 12 and 13

Alternatively, the luminescent donor and luminescent acceptor molecules are synthetic dye molecules and not proteins. Typically these donor and acceptor molecules are covalently attached to each other and subsequently attached to the conjugated substance along with the quencher dye. Alternatively, all three molecules can be encapsulated in a microparticle and are not covalently attached to each other. The microparticle provides an environment wherein the donor and acceptor molecules are in close proximity to facilitate energy transfer when excited at an appropriate wavelength.

Therefore, in another aspect the present compound is part of a composition wherein the composition comprises:
 a) a luminescent donor molecule having a first absorption and emission spectra;
 b) a luminescent acceptor molecule having a second absorption and emission spectra;
 c) a present non-fluorescent compound wherein the non-fluorescent compound accepts fluorescence from the luminescent donor molecule; and,
 d) a carrier molecule that is an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus.

The luminescent donor and present quencher compound are independently covalently bonded or non-covalently associated with the carrier molecule. The luminescent donor and quencher compound may be covalently bonded to the same carrier molecule or alternatively to different carrier molecules that associate with each other. When the donor and quencher acceptor are conjugated to the same carrier molecule the substance is typically cleavable during an assay so that restored signal from the donor molecule indicates the presence of particular analyte, typically an enzyme or protease. In another aspect of the invention, the donor and quencher compound are covalently bonded to different carrier molecules. Typically, the different carrier molecules are members of a specific binding pair that associate non-covalently in such a way to bring the donor and quenching compound within a close proximity. In this way, the composition can be used to detect an analyte of interest, event or ligand either by the quenching of a signal or the restoration of a signal.

Thus, in another aspect of the invention, a carrier molecule may be covalently bonded to exactly one quencher compound of the present invention wherein the composition comprises the following components:
 a) a non-fluorescent quenching compound according to any one compound of the present invention that is an fluorescence energy acceptor molecule; and
 b) a carrier molecule that is an amino acid, a peptide, a protein, a polysaccharide, an antibody, a nucleoside, a nucleotide, an oligonucleotide, a nucleic acid, a hapten, a psoralen, a drug, a biotin-binding protein, a hormone, a lipid, a lipid assembly, a synthetic polymer, a polymeric microparticle, a biological cell or a virus.

The present invention provides for numerous combinations of compositions that comprise at least one quencher compound and a carrier molecule and optionally chromophores that are luminescent donor and luminescent acceptor molecules. These present compositions can be used, without limitation, for the detection of an analyte of interest or to decrease the residual energy from a luminescent donor molecule by methods well known in the art.

The luminescent donor and luminescent acceptor as used herein refer to reporter molecules that are capable of generating a detectable signal and are capable of participating in energy transfer. This energy transfer to a quencher compound of the present invention and/or luminescent acceptor results in the ability to detect, monitor and quantitate an analyte or ligand of interest in a sample. Therefore, reporter molecules are chromophores that include, without limitation, a synthetic dye, a fluorophore, a fluorescent protein, a phosphorescent dye and a chemiluminescent molecule. Preferred reporter molecules include dyes and fluorescent proteins.

In one aspect the luminescent donor molecule is a fluorescent protein, such as phycoerythrin protein. In another aspect, the luminescent acceptor molecule is a fluorescent dye, which is, but is not limited to, xanthene, cyanine, borapolyazaindacene, oxazole, merocyanine, coumarin, pyrene, or indole.

The present reporter molecules can be any reporter molecule known to one skilled in the art. A wide variety of chemically reactive fluorescent dyes that may be suitable for incorporation into the compounds of the invention are already known in the art (RICHARD P. HAUGLAND, MOLECULAR PROBES HANDBOOK OF FLUORESCENT PROBES AND RESEARCH PRODUCTS (2002)). A fluorescent dye of the present invention is any chemical moiety that exhibits an absorption maximum beyond 280 nm that can function as a luminescent donor or acceptor molecule, as described herein.

Dyes of the present invention include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a carbocyanine (including any corresponding compounds in US Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Fluorinated xanthene dyes have been described previously as possessing particularly useful fluorescence properties (Int. Publ. No. WO 97/39064 and U.S. Pat. No. 6,162,931).

Preferred dyes of the invention include xanthene, cyanine, borapolyazaindacene, pyrene, naphthalene, coumarin, oxazine and derivatives thereof. Particularly preferred dyes are xanthenes such as fluorescein, rhodamine and derivatives thereof, and cyanine.

Typically the dye contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, carbocyanine and derivatives thereof.

Selected sulfonated dyes also exhibit advantageous properties, and include sulfonated pyrenes, coumarins, carbocyanines, and xanthenes (as described in U.S. Pat. Nos. 5,132,432; 5,696,157; 5,268,486; 6,130,101). Sulfonated pyrenes and coumarins are typically excited at wavelengths below about 450 nm (U.S. Pat. Nos. 5,132,432 and 5,696,157).

Fluorescent proteins also find use as luminescent donor and acceptor molecules for the present invention. Examples of fluorescent proteins include green fluorescent protein (GFP) and the phycobiliproteins and the derivatives thereof. The fluorescent proteins, especially phycobiliproteins, are particularly useful for creating tandem dye conjugates. Particularly useful fluorescent proteins are the phycobiliproteins disclosed in U.S. Pat. Nos. 4,520,110; 4,859,582; 5,055,556 and the fluorophore bilin protein combinations disclosed in U.S. Pat. No. 4,542,104. Alternatively, two or more fluorophore dyes can function as an energy transfer pair wherein one fluorophore is a donor dye and the other is the acceptor dye including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554.

In one aspect of the invention, the dye or fluorescent protein has an absorption maximum beyond 480 nm. In a particularly useful embodiment, the dye or fluorescent protein absorbs at or near 488 nm to 514 nm (particularly suitable for excitation by the output of the argon-ion laser excitation source) or near 546 nm (particularly suitable for excitation by a mercury arc lamp). In another exemplary embodiment, the dye or fluorescent proteins has a Stokes shift larger than about 20 nm, preferably greater that about 50 nm.

In an exemplary embodiment, the present compounds of the invention are covalently bonded to a solid support. The solid support may be attached to the compound either through one of the above-mentioned R groups, or through a reactive group, if present, or through a carrier molecule, if present. Even if a reactive group and/or a carrier molecule are present, the solid support may be attached through the A, L or B moiety. In exemplary embodiment, at least one member selected from $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{22}$, $R^{23}$, $R^{24}$, $R^{25}$, and $R^{26}$ are a solid support or are attached to a solid support. Preferably, at least one of $R^2$, $R^3$, $R^4$, $R^{12}$, $R^{22}$, $R^{23}$, $R^{24}$, $R^{25}$, and $R^{26}$ is a solid support or is attached to a solid support, wherein at least one of $R^2$, $R^3$, $R^4$, or $R^{12}$ is a solid support or is attached to a solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

Conjugates of components (carrier molecules, including luminescent donor and acceptor molecules, or solid supports), e.g., drugs, peptides, toxins, nucleotides, phospholipids and other organic molecules are prepared by organic synthesis methods using the reactive reporter molecules of the invention, are generally prepared by means well recognized in the art (Haugland, MOLECULAR PROBES HANDBOOK, supra, (2002)). Preferably, conjugation to form a covalent bond consists of simply mixing the reactive compounds of the present invention in a suitable solvent in which both the reactive compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of peptide or protein conjugates typically comprises first dissolving the protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in an aprotic solvent (usually DMSO or DMF) in an amount sufficient to give a suitable degree of labeling when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the reporter molecule or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

Methods of Use

The carbocyanine quencher compounds accept energy from a wide variety of luminescent donor molecules, provided that the quencher compounds and the donor are in sufficiently close proximity for quenching to occur, and that at least some spectra overlap occurs between the emission wavelength of the donor and the absorption band of the quencher compounds. The present compounds are herein referred to as "quenching compounds". This overlap may occur with emission of the donor occurring at a lower or even higher wavelength emission maximum than the maximal absorbance wavelength of the quenching compound, provided that sufficient spectral overlap exists. Energy transfer may also occur through transfer of emission of the donor to higher electronic states of the acceptor, such as from tryptophan residues of proteins to the weaker absorption bands between 300 and 350 nm typical of the dyes in the ultraviolet region. Preferably, the quenching compound of the invention is only dimly fluorescent, or essentially nonfluorescent, so that energy transfer results in little or no fluorescence emission.

Typically, quenching occurs through Fluorescence Resonance Energy Transfer between a donor and a quenching acceptor of the invention. The degree of FRET exhibited by a donor acceptor pair can be represented by the Förster equation. Because the degree of energy transfer is dependent on the spectral overlap, it can be readily appreciated that the spectral properties of the luminescent donor and acceptor molecules have a strong effect on the energy transfer observed. It should be readily appreciated that the degree of energy transfer during FRET, and therefore quenching, is highly dependent upon the separation distance between the luminophore and the quenching compound. In molecular systems, a change in luminescence quenching typically correlates well with a change in the separation distance between the luminophore molecules and the quenching compound molecules. Assays that detect such changes in luminescence are therefore useful for the detection of a great many structural changes, such as changes in molecular conformation, assembly of structures, or degradation of structures.

Therefore, the present quenching compounds find use as traditional quenchers of luminescent donor molecules wherein the restoration or absence of a signal indicates the analyte or ligand of interest. These many and varied uses are descried below. However, we have unexpectedly found that the present compounds can be used in conjunction with an energy transfer pair as an intermediate to accept the fluorescence from the donor molecule that was not accepted by the luminescent acceptor molecule. This is a new method wherein the quenching compound is not used to quench to donor signal but to accept the residual fluorescence from the donor such that this residual fluoresces peak does not need to be compensated for when using flow cytometry-based applications. The use of tandem conjugates in flow cytometry-based assays is employed so that a large Stokes shift is obtained. This is important because it shifts the detectable signal farther away from the range that autofluorescence is observed in biological samples and because it provides the ability to use another non-tandem labeled conjugate for the detection of another target analyte. However, if there is a significant amount of fluorescence that is not absorbed by the acceptor molecule that a second visible signal is detected. This second signal can be compensated for using filters. However, using the present quenching compounds, the need for this compensation is reduced, simplifying the use of tandem conjugates, especially conjugates comprise R-PE.

Thus, in one aspect of the invention, a presently preferred method for absorbing residual energy from an energy donor molecule during energy transfer between a luminescent donor molecule and a luminescent acceptor molecule comprises the following steps:
 a) covalently bonding a luminescent donor molecule to a luminescent acceptor molecule to prepare an energy transfer pair;
 b) covalently bonding a present cyanine quenching compound to the energy transfer pair to prepare a quencher labeled energy transfer pair;

c) covalently bonding the quencher labeled energy transfer pair to a carrier molecule to prepare a ternary labeled carrier molecule;

d) illuminating the ternary labeled carrier molecule with an appropriate wavelength wherein fluorescence from the luminescent donor molecule is accepted by the luminescent acceptor molecule and the residual fluorescence from the luminescent donor molecule is accepted by the quenching compound whereby the residual energy is absorbed during energy transfer between the luminescent molecules.

The luminescent donor molecule and the luminescent acceptor molecule are typically conjugated to each other first to form an energy transfer pair. Subsequently the present quenching compound is covalently bonded to the energy transfer pair to form a quencher labeled energy transfer pair. However, the order in which the luminescent donor molecule, luminescent acceptor molecule and quenching compound are covalently bonded to each other can be changed. Typically, this ternary compound is formed first before covalently bonding to the carrier molecule so that the donor, acceptor and quencher compound are within proximity to participate in FRET. Typically, the carrier molecule is a member of a specific binding pair that can be used to detect an analyte of interest in a sample.

The compositions (quencher labeled energy transfer pair and ternary labeled carrier molecules) and methods for absorbing residual energy can be further used to detect an analyte of interest in a sample.

Therefore, a method for detecting the presence or absence of an analyte of interest in a sample comprises the following steps:

a) contacting the sample with a composition to form a labeled sample, wherein the composition comprises a carrier molecule, a luminescent donor molecule, a luminescent acceptor molecule and a present cyanine quenching acceptor molecule;

b) incubating the labeled sample for a sufficient amount of time for the carrier molecule to associate with the analyte to form an incubated sample;

c) illuminating the incubated sample with an appropriate wavelength to form an illuminated sample; and d) observing the illuminated sample whereby the analyte in the sample is detected.

The composition comprises at least one quencher compound of the present invention, but may comprise a reporter molecule that is a luminescent donor and/or a luminescent acceptor. The composition can be used to detect the analyte of interest directly wherein the conjugated substance is a member of a specific binding pair that binds the analyte of interest or the conjugated substance is a substrate for the analyte of interest or is displaced by the analyte of interest. Alternatively, the composition is used in the above method to indirectly detect an analyte of interest wherein the conjugated substance is a biotin-binding protein, or the like, that does not bind directly to the analyte of interest.

In another exemplary embodiment, the present quenching compounds are covalently bonded to a carrier molecule, which may additionally comprise a luminescent donor molecule, depending on the intended assay. Thus, the quenching compounds of the invention are useful in any application where energy transfer from a luminescent donor to a non-fluorescent acceptor has previously been described, provided that some spectral overlap exists between the emission of the donor dye and the absorbance of the quenching compound of the invention. In this instance, the quenching compounds are used in combination with a luminophore in a method that detects a change in separation distance between the luminophore and the quenching compound.

The luminescent donor molecules and quenching compounds used in the present methods are useful in any medium in which they are sufficiently soluble. For example, selected embodiments of the present quenching compounds that are substituted by highly non-polar substituents may be useful in organic solvents, or on or in non-polar matrices, such as polymeric microspheres. For biological applications, the quenching compounds of the invention and their conjugates are typically used in an aqueous, mostly aqueous or aqueous-miscible solution prepared according to methods generally known in the art.

In one embodiment, the quencher labeled carrier molecule is utilized in a homogenous solution assay, where specific spatial resolution is not required. In these embodiments, the loss of, or restoration of, luminescence in the sample is detected. In another embodiment, the quenching compound forms a covalent or non-covalent association or complex with an element of the sample where a luminescent component is present or is subsequently added. In this embodiment, illumination of the sample reveals either a luminescence response if quenching is not occurring, or the degree of quenching may be observed and correlated with a characteristic of the sample. Such correlation typically occurs by comparison with a standard or a calibration curve. Typically, a stained sample is illuminated and observed in order to determine a specified characteristic of the sample by comparing the degree of quenching exhibited to a luminescence standard of determined intensity. The luminescence standard may be a fluorescent dye such as the fluorophore used to prepare the quenching compound-fluorophore labeled carrier molecule, a luminescent particle (including fluorescent microspheres), a calibration curve prepared by assaying the doubly labeled substance with a known amount of enzyme or degradation activity, or any other standard that can be used to calibrate luminescence signal intensity as well known in the art.

In one aspect, the present method for detecting the separation distance between one or more luminescent donor molecules and a quencher compound, comprises the steps:

a) contacting a sample with a present cyanine labeled carrier molecule to prepare a labeled sample;

b) incubating the labeled sample for a sufficient amount of time to prepare an incubated sample c) illuminating the incubated sample with an appropriate wavelength;

d) detecting a first luminescence response of the sample, which yields information as to the separation distance of one or more luminescent donors and quenching compound acceptors;

e) exposing the sample to an environmental condition sufficient to change the separation distance, or thought to be sufficient to change the separation distance;

f) illuminating the sample;

g) detecting the second luminescence response of the sample; and h) comparing the first detected luminescence response to the second detected luminescence response, to determine a detectable difference in the detected luminescence before and after the exposure to the selected environmental condition.

The detected change in the luminescence of the sample then correlates with any changes that occurred in the separation distance between the luminescent donor molecule and the quenching compounds, typically in response to the selected environmental condition. The environmental condition of the instant method may be the presence of a particular enzyme, the presence of a complementary specific binding pair member, a change in pH, or a change in sample temperature.

In one embodiment, the method of the instant invention is utilized to detect molecular or structural assembly (convergence). In another embodiment, the method of the invention is utilized to detect molecular or structural disassembly (divergence). In yet another embodiment, the method of the invention is utilized to detect a conformation change in a molecule, macromolecule or structure (optionally convergence or divergence). In yet another embodiment, the method of the instant invention incorporates aspects of the detection of assembly, disassembly, and/or conformation changes.

In one embodiment, the luminescence of a luminescent donor molecule becomes quenched upon being placed in close proximity to a quenching compound of the invention (thereby decreasing the separation distance). The following systems, among others, can be analyzed using energy transfer pairs to detect and/or quantify structural assembly by measuring convergence of the donor and acceptor: protein subunit assembly; enzyme-mediated protein assembly; molecular dimensions of proteins; membrane-protein interactions; protein-protein interactions; protein-protein-nucleic acid complex assembly; receptor/ligand interactions; immunoassays; nucleic acid hybridization; quantitative detection of specific DNA sequence amplification; detection of DNA duplex winding; nucleic acid-protein interactions; nucleic acid-drug interactions; primer extension assays for mutation detection; reverse transcriptase assay; strand exchange in DNA recombination reactions; membrane fusion assays; transmembrane potential sensing; and ligation assays.

In particular, specific binding pair members labeled with a quenching compound are typically used as probes for the complementary member of that specific binding pair, by methods well known in the art. The complementary member is typically labeled with a luminescent donor molecule, and association of the two members of the specific binding pair results in luminescence quenching. This assay is particularly useful in nucleic acid hybridization assays, evaluation of protein-nucleic acid interaction, and in selected standard immunoassays. In one embodiment, a loss of luminescence indicates the association of an enzyme with an enzyme substrate, agonist or antagonist, such that the luminophore on one is brought into close proximity to a quenching compound on the other. Selected preferred specific binding pair members are proteins that bind non-covalently to low molecular weight ligands (including biotin, oligonucleotides, and drug-haptens.

Alternatively, a monomer, labeled with a quenching compound, is incorporated into a polymer labeled with a luminescent donor molecule, resulting in quenching of luminescence. In particular, a quenching compound-labeled nucleotide can be incorporated via the polymerase chain reaction into a double stranded DNA molecular that is labeled with a luminescent donor molecule.

In another embodiment of the method of the invention, the disassembly, cleavage or other degradation of a molecular structure is detected by observing the partial or complete restoration of luminescence of a luminescent donor molecule. Typically, the initially quenched luminescence of a luminophore associated with the structure becomes dequenched upon being released from the constraint of being in close proximity to a quenching compound of the invention. The quenching compound is optionally associated with the same molecular structure as the luminophore, or the donor and acceptor are associated with adjacent but distinct subunits of the structure. The following systems, among others, can be analyzed using energy transfer pairs to detect and/or quantify structural disassembly: detection of protease activity using fluorogenic substrates (for example HIV protease assays); detection of enzyme-mediated protein modification (e.g. cleavage of carbohydrates/fatty acids, phosphates, prosthetic groups); immunoassays (via displacement/competitive assays); detection of DNA duplex unwinding (e.g. helicase/topoisomerase/gyrase assays); nucleic acid strand displacement; ds DNA melting; nuclease activity; lipid distribution and transport and TAQMAN assays.

Structure disassembly is typically detected by observing the partial or complete restoration of luminescence, as a carrier molecule is exposed to a degradation condition of interest for a period of time sufficient for degradation to occur. A restoration of luminescence indicates an increase in separation distance between the luminophore and quenching compound, and therefore a degradation of the carrier molecule. If the detectable difference in luminescence is detected as the degradation proceeds, the assay is a continuous assay. Since most enzymes show some selectivity among substrates, and as that selectivity can be demonstrated by determining the kinetic differences in their hydrolytic rates, rapid testing for the presence and activity of the target enzyme is provided by the enhancement of luminescence of the labeled carrier molecule following separation from the quenching compound.

In another embodiment of the invention, a single-stranded oligonucleotide signal primer is labeled with both a quenching compound and a fluorescent donor dye, and incorporates a restriction endonuclease recognition site located between the donor dye and the quenching compound. The single-stranded oligonucleotide is not cleavable by a restriction endonuclease enzyme, but upon binding to a complementary (target) nucleic acid, the resulting double stranded nucleic acid is cleaved by the enzyme and the decreased quenching is used to detect the presence of the complementary nucleic acid (U.S. Pat. No. 5,846,726).

In yet another embodiment of the invention, structural disassembly can be detected by the quenching of luminescence. In this embodiment, the action of an oxidative enzyme on a colorless precursor results in the generation of a quenching compound of the invention. The newly generated quenching compound then quenches the luminescence of a luminophore if it is in sufficiently close proximity, indicating the presence and/or activity of the enzyme.

A single nucleotide polymorphism (SNP) can be detected through the use of sequence specific primers, by detection of melt temperatures of the double stranded nucleic acid. In this aspect, the complementary or substantially complementary strands are labeled with a quenching compound and a luminescent donor molecule, respectively, and dissociation of the two strands (melting) is detected by the restoration of luminescence of the donor.

In yet another example of a divergence assay, the rupture of a vesicle containing a highly concentrated solution of luminophores and quenching compounds is readily detected by the restoration of luminescence after the vesicle contents have been diluted sufficiently to minimize quenching.

In another exemplary embodiment, a conformational change is measured. In this embodiment, the quenching compound and the luminescent donor molecule are present on the same or different substances, and a change in the three-dimensional structural conformation of one or more components of the assay results in either luminescence quenching or restoration of luminescence, typically by substantially decreasing or increasing the separation distance between the quenching compound and a luminophore. The following systems, among others, can be analyzed using energy transfer pairs to detect and/or quantify conformation changes: protein conformational changes; protein folding; structure and conformation of nucleic acids; drug delivery; antisense oligonucleotides; cell-cell fusion (e.g. via the diffusion apart of an initial donor-quenching compound pair)

By conformation change is meant, for example, a change in conformation for an oligonucleotide upon binding to a complementary nucleic acid strand. In one such assay, labeled oligonucleotides are substantially quenched when in solution, but upon binding to a complementary strand of nucleic acid become highly fluorescent (often referred to as "Molecular Beacons", as described in EP 0 745 690; and U.S. Pat. Nos. 5,925,517 and 6,103,476). Another example detects the change in conformation when an oligonucleotide that has been labeled at its ends with a quenching compound and a luminophore, respectively, loses its G-quartet conformation upon hybridization to a complementary sequence, resulting in decreased luminescence quenching (U.S. Pat. No. 5,691,145). Alternatively, the binding of an enzyme substrate within the active site of a labeled enzyme may result in a change in tertiary or quaternary structure of the enzyme, with restoration or quenching of luminescence.

In another exemplary embodiment, the present quenching compounds are used to decrease the background fluorescence from nucleic stains that used to detect nucleic acid in a sample (U.S. Pat. No. 6,323,337). In this instance the quenching compounds are covalently bonded to an oligonucleotide (herein referred to as a "quenching oligonucleotide") and the nucleic acid stain is the luminescent donor. By nucleic acid stain is meant a dye compound that associates non-covalently with nucleic acid, which are well known in the art. In one aspect the quenching oligonucleotides can be used to reduce the background fluorescence of a hybridization event that is detected with a nucleic acid stain that associates non-covalently with the nucleic acid, wherein the nucleic acid stain is the luminescent donor molecule. In this particular application, the covalently bound acceptor moiety to the oligonucleotide decreases the fluorescence of non-covalently associated fluorescent nucleic acid stains. This is particularly useful when the oligonucleotide is a primer for a nucleic acid amplification or elongation reaction. In this instance, the quenching oligonucleotides possess utility for decreasing background fluorescence. This background fluorescence is typically due to the binding of nucleic acid stains to oligonucleotide primers used in primer extension, reverse transcription, DNA polymerization, RNA polymerization and other primed strand elongation processes. The quenched oligonucleotides are particularly useful for reducing background fluorescence due to the staining of primer dimers present during amplification assays. The present cyanine compounds covalently bonded to a oligonucleotide "quenching oligonucleotide" are also useful for decreasing the fluorescence background in enzyme assays, by reducing the fluorescence that would otherwise arise from binding of nucleic acid stains to ligase substrates, or nuclease substrates.

The combination of quenching oligonucleotides and luminescent nucleic acid stains are useful in any application where it is desirable to minimize the fluorescent signal from selected oligonucleotides used in the application. In one aspect of the invention, the quenching oligonucleotides, comprising a present cyanine compound as a quencher, are used in conjunction with a reaction mixture for performing the polymerase chain reaction (PCR), real-time PCR, the strand displacement assay (SDA), the ligase chain reaction (LCR), nucleic acid sequence-based amplification (NASBA), Q beta replicase-based amplification, cycling probe reaction (CPR), solid phase amplification (SPA) or self sustained sequence replication (3SR) to decrease background fluorescence upon staining the amplified product mixture with a fluorescent nucleic acid stain. For example, when the quenching oligonucleotides are used as the primers in the PCR amplification, background fluorescence from residual primers or dimers of residual primers is essentially eliminated, resulting in substantially more accurate determination of the amount of amplified product sequence present in the amplification mixture.

In another aspect of the invention, the combination of quenching oligonucleotides and fluorescent nucleic acid stains is used to assay for the presence or absence of a selected protein. This method typically requires preparing a mixture comprising a quenching oligonucleotide and a nucleic acid stain such that the nucleic acid stain associates noncovalently with the oligonucleotide with concomitant quenching of the luminescence of the nucleic acid stain. To this mixture is added a sample that contains or is suspected of containing a protein of interest. After incubation of the mixture it is illuminated and the resulting luminescence is correlated with the presence or activity of the protein of interest, typically by comparison with a calibration curve, or with luminescence values obtained for positive or negative controls.

In one aspect, the protein is an enzyme, such as a ligase or nuclease. Where the quenching oligonucleotide is exposed to a nuclease enzyme (e.g. DNAse or RNase) in the presence of a fluorescent nucleic acid stain, initial cleavage of the oligonucleotide by a nonspecific endonuclease results in oligonucleotide fragments that are no longer in proximity to the quenching moiety, but that still bind nucleic acid stain to become fluorescent. Fluorescence initially increases but, with additional exposure to the nuclease, the fluorescent signal decreases, providing an indication of the presence of the nuclease enzyme, the enzyme activity, and the rate of enzymatic cleavage.

Certain nucleases, such as restriction endonucleases, recognize specific sequences in double- or single-stranded nucleic acids, or have a strong preference for cleaving at sites containing only purines or only pyrimidines. Where the quenching oligonucleotide comprises a cleavage site for a site-specific nuclease, then cleavage at that site releases a nucleic acid fragment that is no longer in proximity to the quenching moiety but that still binds a nucleic acid stain to become fluorescent. The fluorescence of the fragment containing the quenching moiety is not fluorescent, and the intact template is not fluorescent. Measuring the resulting increase in fluorescence after treatment with the enzyme provides an accurate measure of the relative activity, presence and abundance of the nuclease.

Selected enzymes, such as exonucleases, cleave single nucleotides from either the 3'- or 5'-terminus of the oligonucleotide. Where the quenched oligonucleotide of the invention is sufficiently long, the nucleic acid stains that are associated with the oligonucleotide at sufficient distance from the quenching moiety will exhibit substantial fluorescence. As nucleotides are cleaved from the terminus distant from the quenching moiety, overall fluorescence will decrease, until the shortened oligonucleotide becomes essentially nonfluorescent, thus providing a measure of the activity or abundance of the enzyme.

Certain proteins and complexes recognize specific sequences in single- or double-stranded nucleic acids. If such a sequence is incorporated into a quenching oligonucleotide, then binding of the cognate factor disrupts transfer of energy from the donor nucleic acid stain to the quenching moiety. This disruption is achieved by changing the flexibility or rigidity of the nucleic acid, thus affecting the interaction between the dyes, or by affecting the secondary structure of the nucleic acid, thus affecting the angle of the resulting dipoles of the donor and quencher dyes with respect to one another. Since some nucleic acid binding proteins (binding factors) bend DNA significantly upon binding, the resulting bound nucleic acid stains are quenched less upon binding. Other environmental factors also affect the secondary and/or tertiary structure of the quenching oligonucleotide, such as the presence of specific enzymes, a complementary strand of nucleic acid, or an increase in temperature. As loss of secondary or tertiary structure typically places associated nucleic acid stain molecules at a greater distance from the quenching moiety, overall luminescence quenching is reduced. In this way, the environmental factor of choice may be detected or quantitated.

In another aspect, the quenched oligonucleotide primers are used to reduce background fluorescence when the primers are used for template-directed strand elongation by DNA or RNA polymerases or reverse transcriptases and elongation products are detected using nucleic acid stains. In such assays, the quenched oligonucleotide primer is elongated by addition of nucleotides (usually to the 3' terminus of the primer) by the appropriate enzyme, usually in a template-directed manner. Enzymes such as terminal deoxynucleotidyl transferase add nucleotides to a primer in a non-template directed manner, but can be assayed in the same way. The nucleic acid stain that associates with the primer is essentially non-fluorescent or exhibits strongly diminished fluorescence, but when the oligonucleotide is extended sufficiently, associated nucleic acid stains are no longer efficiently quenched and the oligonucleotide becomes more strongly fluorescent. The rate at which fluorescence arises and the amount of resulting fluorescence are measures of the activity or abundance of the enzyme in the sample.

In yet another aspect, the quenched single- or double-stranded oligonucleotides are used to reduce the background fluorescence in assays for DNA or RNA ligases, splicing enzymes, or telomerases when the products of such reactions are detected using nucleic acid stains. In these assays, the enzyme of interest catalyzes the formation of a covalent bond between the two termini of single- or double-stranded nucleic acids. Some enzymes, such as T4 DNA ligase, form covalent linkages between double-stranded DNA fragments. Other enzymes, such as T4 RNA ligase, form covalent linkages between single-stranded DNA or RNA fragments. In these assays, there are two single- or double-stranded oligonucleotides used as substrates. One oligonucleotide of the invention is labeled at one terminus and the other oligonucleotide is not labeled. Nucleic acid stains associated with the unlabeled oligonucleotide are fully fluorescent, while nucleic acid stains associated with the quenching moiety-labeled oligonucleotide are essentially nonfluorescent or exhibit strongly diminished fluorescence. When the enzyme joins the two oligonucleotides, the resulting ligation product exhibits decreased fluorescence when stained, relative to the non-ligated oligonucleotides. The resulting decrease in fluorescence or the rate of decrease is a measure of the activity or abundance of the enzyme in the sample.

In another aspect, the quenched single-stranded oligonucleotides are used in hybridization assays, in which the products of hybridization are detected using nucleic acid stains. Single-stranded oligonucleotides bind nucleic acid stains of the invention and form fluorescent complexes. When those single-stranded oligonucleotide complexes hybridize to probes that have an acceptor coupled to them, the fluorescence of the associated nucleic acid stains is quenched relative to those associated with the original complex. Thus hybridization can be monitored as a decrease in fluorescence. This fluorescence decrease can be used as a measure of the abundance of the target nucleic acid in the original sample, of the presence or absence of a target nucleic acid, or of the sequence of the target nucleic acid, if hybridization conditions are chosen appropriately. For example, a single mismatch or single base polymorphism or mutation can be identified as the lack of fluorescence decrease upon exposure of the sample to hybridization conditions, due to lack of resulting formation of the hybrid. Even large single-stranded target sequences can be identified in this way, as long as the observed decrease in fluorescence is large enough to ensure that the measurement is accurate, relative to the background of unhybridized fluorescent target nucleic acid.

Sample Preparation

The end user will determine the choice of the sample and the way in which the sample is prepared. The sample includes, without limitation, any biological derived material that is thought to contain an analyte of interest. Alternatively, samples also include material that an analyte of interest has been added to determine the effect the analyte has on predetermined biological parameters. In another aspect of the invention, the sample can also include a buffer solution that contains any of the quencher compositions of the present invention to determine the ability of the carbocyanine compounds to quench the donor signal or the ability to reduce the residual energy from the donor molecule in the absence of an analyte or ligand.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, β cells, hepatocytes, and neurons.

In one aspect the sample comprises live cells, intracellular fluids, extracellular fluids, biological fluids, biological fermentation media, environmental sample, industrial samples, proteins, peptides, buffer solutions biological fluids or chemical reactors. In a further aspect, the sample comprises blood cells, immune cells, cultured cells, muscle tissue, neurons, extracellular vesicles; vascular tissue, blood fluids, saliva, urine; water, soil, waste water, sea water, pharmaceuticals, foodstuffs or beverages.

In one aspect the sample may be immobilized in or on a solid or semi-solid matrix. In this instance the sample may be immobilized on a polymeric membrane, within a polymeric gel, on a microparticle, on a microarray, on a silicon chip, on a glass slide, on a microwell plate, or on a microfluidic chip.

Illumination

The sample and or quencher compositions are illuminated with a wavelength of light selected to give a detectable optical response, and observed with a means for detecting the optical response. Equipment that is useful for illuminating the present compounds and compositions of the invention includes, but is not limited to, hand-held ultraviolet lamps, mercury arc lamps, xenon lamps, lasers and laser diodes. These illumination sources can be optically integrated into laser scanners, fluorescence microplate readers, flow cytometers or standard or microfluorometers.

The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Kits of the Invention

Embodiments of the invention also include suitable kits for labeling a carrier molecule and detecting a ligand (analyte of interest). Such kits can be prepared from readily available materials and reagents and can come in a variety of embodiments. The contents of the kit will depend on the design of the assay protocol or reagent for detection or measurement. All kits will contain instructions, appropriate reagents, present quencher compounds. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above.

A kit for labeling a substance and forming a quencher conjugated substance typically comprises a non-fluorescent quenching compound according to the present invention, instructions for conjugating said non-fluorescent quenching compound to said substance; and optionally one or more of the following; a buffering agent, a purification medium, a sample of said substance, an organic solvent, and one or more reporter molecules. This kit allow the end user to make many of the compositions contemplated by the present invention that can then be used to detect a ligand in a sample.

Another kit of the invention includes a kit for detecting a ligand in a sample. Typically, this kit would comprise a composition according to the present invention and instructions for detecting said ligand. The composition is typically a non-fluorescent carbocyanine conjugate wherein the carrier molecule is typically a member of a specific binding pair.

Those skilled in the art will appreciate that a wide variety of additional kits and kit components can be prepared according to the present invention, depending upon the intended user of the kit, and the particular needs of the user.

A detailed description of the invention having been provided above, the following examples are given for the purpose of illustrating the invention and shall not be construed as being a limitation on the scope of the invention or claims.

EXAMPLES

Example 1

Preparation of Compound 1

A mixture of 2 g of 1,2,3,3-3H-tetramethylindolium iodide and 1.6 g of terephthalic acid monomethyl ester chloride is heated in 20 mL of pyridine at 45 C overnight. The solvent is evaporated under reduced pressure and the crude product is purified on a silica gel column to give compound 1.

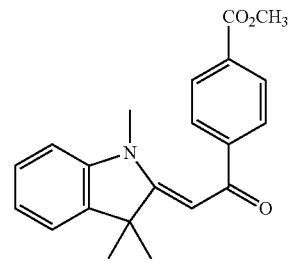

Compound 1

Example 2

Preparation of Compound 2

A mixture of 200 mg of Compound 1 and 0.18 mL of phosphorous oxychloride is heated in 5 mL of dichloroethane at reflux for 2 hours to generate the [2-chloro-2-(4-methoxycarbonylpheny)]vinyl-1,3,3-trimethylindolium chloride. This intermediate is then stirred with 0.3 g of 1-(5-carboxypentyl)-5-sulfo-2,3,3-trimethylindolium inner salt and 0.22 mL of triethylamine in several mL of DMF at room temperature overnight. The crude product is precipitated out by the addition of ethyl acetate and then purified by HPLC to give compound 2.

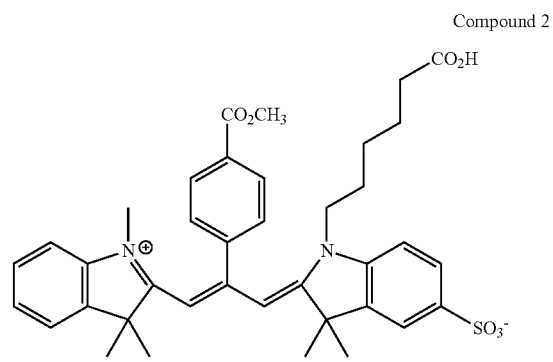

Compound 2

Example 3

Preparation of Compound 3

The [2-chloro-2-(4-methoxycarbonylpheny)]vinyl-1,3,3-trimethylindolium chloride is reacted with one equivalent of 2,3-dimethylbenzothiazolium tosylate and 3 equivalents of triethylamine in dichloroethane to obtain Compound 3.

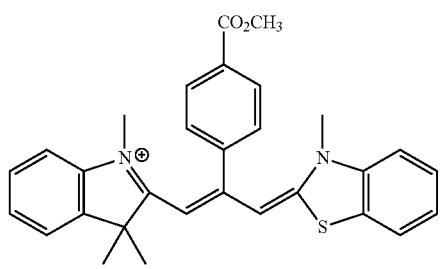

Compound 3

Example 4

Preparation of compound 4

A mixture of about 0.3 mmole of [2-chloro-2-(4-methoxycarbonylpheny)]vinyl-1,3,3-trimethylindolium chloride, 0.6 mmole of 3,(5-carboxypentyl)-5-sulfo-1,2,3-trimethylindolium inner salt, and 0.22 mL of triethylamine is stirred in several mL of DMF overnight. The crude product is precipitated out by the addition of ethyl acetate and purified by silica gel chromatography to give compound 4.

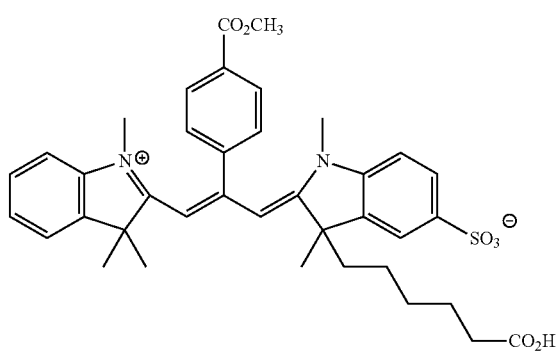

Compound 4

Example 5

Preparation of Compound 5

A mixture of about 0.38 mmole of [2-chloro-2-(4-methoxycarbonylpheny)]vinyl-1,3,3-trimethylindolium chloride, one equivalent of 1,2,3,3-3H-tetramethylindolium iodide, and 3 equivalents of triethylamine is stirred in 5 mL of dichloroethane at room temperature for 30 minutes. The reaction mixture is washed with water and dried over magnesium. The crude residue is then stirred in ethyl acetate to yield compound 5.

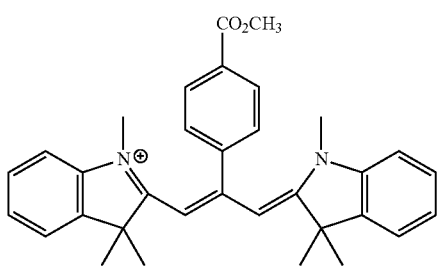

Compound 5

Example 6

Preparation of Compound 6

To a mixture of 33 mg of Compound 2 and 0.2 mL of triethylamine in 1 mL of DMF at room temperature, is added 23 mg of O—[N-succinimidyl]-N,N,N',N'-tetramethyluronium tetrafluoroborate and the mixture is stirred for 2 hours. At the end of the period, ether is added to precipitate out compound 6.

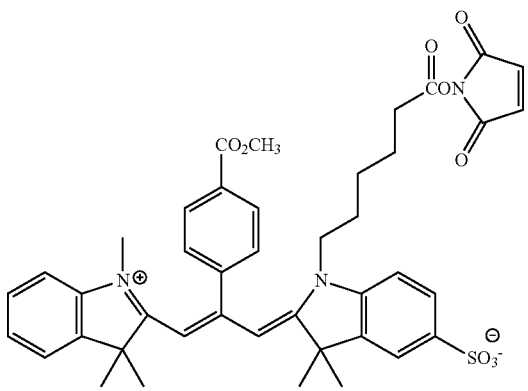

Compound 6

Example 7

Preparation of Compound 7

A mixture of 0.3 mmole of (2-chloro-2-phenyl)vinyl-1,3,3-trimethylindolium chloride, one equivalent of 1,2-dimethylquinolinium tosylate and 5 equivalents of triethylamine is stirred in 5 mL of dichloroethane for 30 minutes to generate Compound 7.

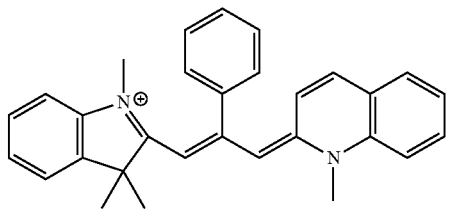

Compound 7

Example 8

Preparation of Energy Transfer Pair (R-Phycoerythrin (R-PE) and Compound 6) Protein Conjugate and Demonstration of R-PE Quenching by Compound 6

0.5 mL (5 mg) of a 10 mg/mL solution of R-PE in 0.1 M sodium phosphate, 0.1 M sodium chloride buffer, pH 7.5 was reacted with a 6, 10, or 18-fold molar excess of Compound 6 at 10 mg/mL in anhydrous dimethylsulfoxide (DMSO) for 1.5 hours at room temperature (RT). The dye-protein conjugates were separated from free dye by size exclusion chromatography using 3-1.5×10 cm columns packed with Bio-Rad™ Bio-Gel® P-30 fine in 0.1M sodium phosphate, 0.1 M sodium chloride buffer, pH 7.5 and eluted with same.

The initial protein-containing band from each column was collected. The absorbance spectra were obtained on a Perkin-Elmer Lambda 35 UV/VIS spectrometer. The fluorescence emission spectra were obtained using an Aminco Bowman Series 2 Luminescence Spectrometer, excited at 488 nm. The conjugates show a quenching at 575 nm of 84.4%, 95.2%, and 98.6% respectively, compared to unmodified R-PE excited at the same wavelength. See, FIG. 1.

Example 9

Preparation of Energy Transfer Pair (R-PE-Alexa Fluor® 750, Succinimidyl Ester (SE)) with Compound 6 Protein Conjugate 0.8 mL (8 mg) of R-PE labeled with Compound 6 as in example 8, was secondarily labeled with Alexa Fluor® 750, SE using a 20-fold excess of SE at 10 mg/mL in anhydrous DMSO and reacted 1 hour at RT. The reaction was stopped by removal of excess free dye as in example 8.

Figure 2:
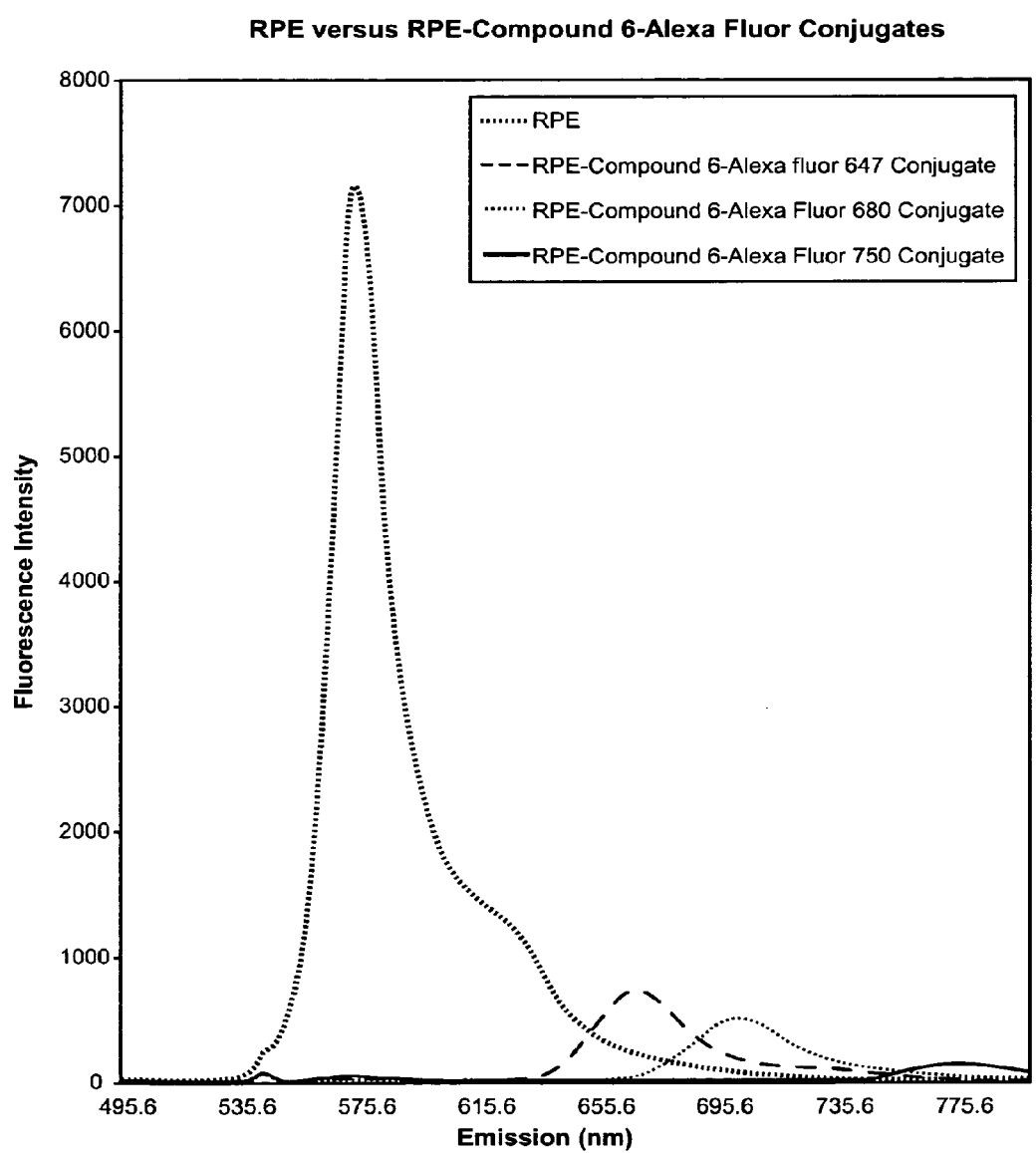
FIG. 2: Shows the ability of compound 6 to quench the residual fluorescence of the R-PE (donor) and improve the overall energy transfer efficiency wherein the R-PE emitted energy is accepted by both the quencher (Compound 6) and the fluorescent acceptor (Alexa Fluor 647, 680 and 750 Dyes) when excited at 488 nm. This additional transfer to Compound 6 reduces the residual fluorescence of the donor (R-PE). The energy transfer efficiency between the fluorescent donor and acceptor when excited at 488 nm is 93%, (Em 575/Em 667=0.064) for R-PE-compound 6-Alexa Fluor 647 Dye, 93% (Em 575/Em 703=0.063) for R-PE-compound 6-Alexa Fluor 680 Dye and 67% (Em 575/Em 778=32.6) for R-PE-compound 6-Alexa Fluor 750 Dye. See Examples 9-11.
Figure 3A:
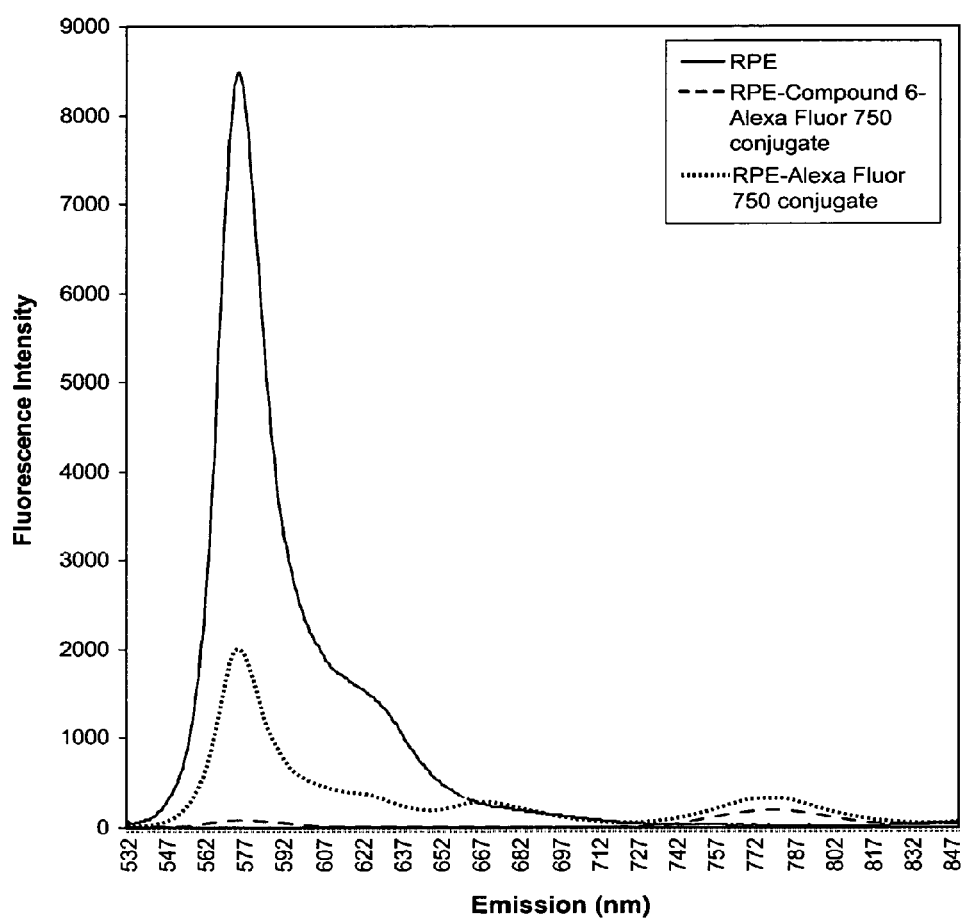
FIG. 3A, FIG. 3B: Shows the comparison of the emission spectra from R-PE alone, R-PE-compound 6-Alexa Fluor 750 Conjugate and R-PE-Alexa Fluor 750 Conjugate (FIG. 3A) and R-PE alone, R-PE-Compound 6-Alexa Fluor 680 Conjugate and R-PE-Alexa Fluor 680 conjugate (FIG. 3B). This figure shows the residual fluorescence from R-PE that is emitted when Compound 6 is not part of the energy transfer tandem conjugate and the residual fluorescence emission that is transferred to Compound 6 when part of the energy transfer conjugate resulting in a primary peak at a longer wavelength that is easily distinguishable over background and from the R-PE residual fluorescence emission.
Figure 3B:
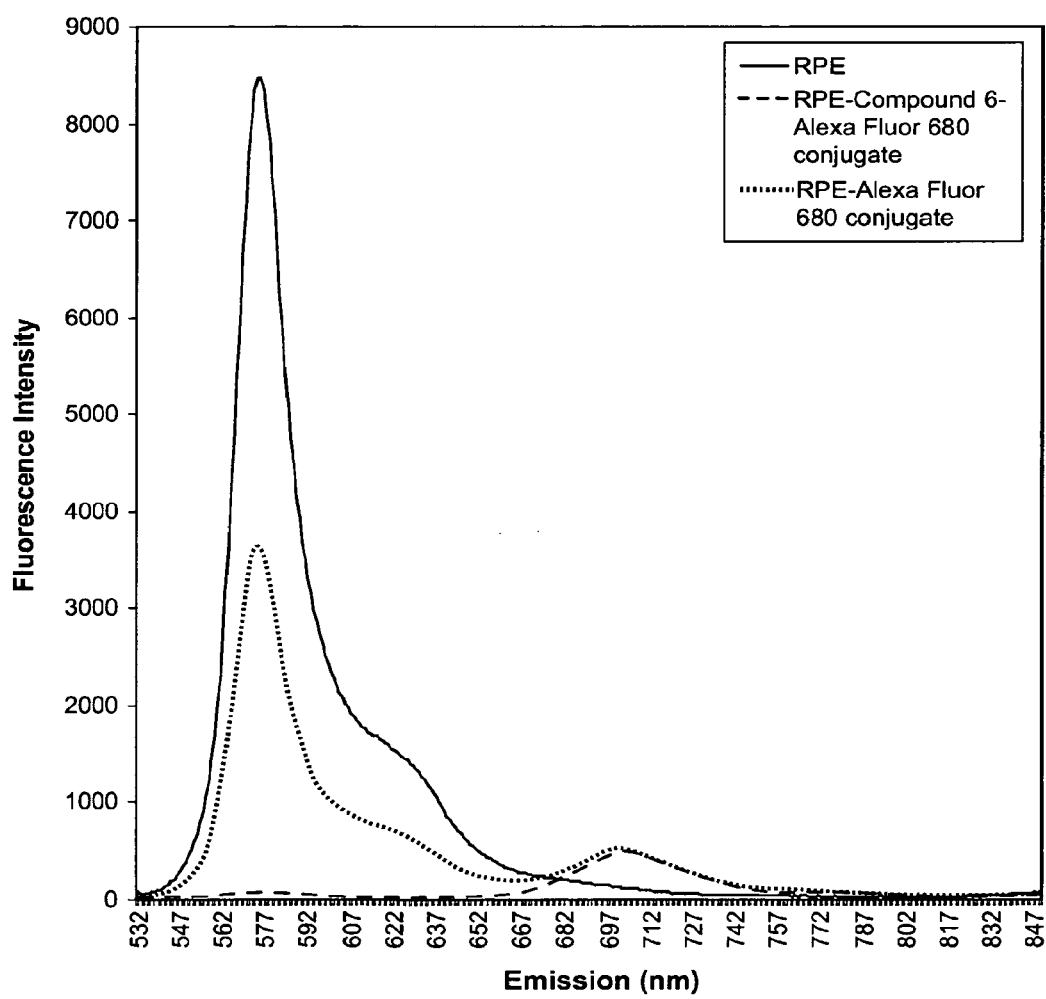

The corrected fluorescence emission spectra of the conjugates were collected on a Hitachi F-4500 Fluorescence Spectrophotometer. When excited at 488 nm, the energy transfer efficiency (Em575/Em778=32.6) was 67%; see, FIG. 2. This complex was conjugated to streptavidin as described by Haugland (METH. MOL. BIOL. 45, 205 (1995)) and analyzed by flow cytometry; See, Example 12.

Example 10

Preparation of Energy Transfer Pair (R-PE-Alexa Fluor® 680, SE) with Compound 6 Protein Conjugate 0.8 mL (8 mg) of R-PE labeled with Compound 6 as in example 8, was secondarily labeled with Alexa Fluor®680, SE using a 20-fold excess of at 10 mg/mL in anhydrous DMSO, reacted at RT for 1 hour. The reaction was stopped by the removal of free dye as described in example 8.

Corrected fluorescence emission spectra excited at 488 nm and collected on a Hitachi F-4500 Fluorescence Spectrophotometer, showed fluorescence resonance energy transfer (FRET) efficiency (Em 575/Em 703=0.063) to be 93%. This complex was conjugated to streptavidin as noted in example 9 and analyzed by flow cytometry; See Example 13.

Example 11

Preparation of Energy Transfer Pair (R-PE-Alexa Fluor® 647, SE) with Compound 6 Protein Conjugate 0.8 mL (8 mg) of R-PE labeled with Compound 6 as in example 8, was secondarily labeled with Alexa Fluor® 647, SE using a 25-fold excess of SE at 10 mg/mL in anhydrous DMSO and reacted 1 hour. The reaction was stopped by the removal of free dye as described in example 8.

Corrected fluorescence emission spectra were collected using a Hitachi F-4500. When excited at 488 nm the FRET (Em 575/Em 667=0.064) efficiency was 93%. This complex was conjugated to streptavidin as noted in example 9, and analyzed by flow cytometry;

Example 12

Energy Transfer Pair (Alexa Fluor®750-R-Phycoerythrin) with Compound 6 Conjugated to Streptavidin Used to Detect CD8 on Human Peripheral Blood Mononuclear Cells (PBMC)

Human Peripheral Blood was drawn into a Cell Preparation Tube (Becton Dickinson, Franklin Lakes, N.J.). Human PBMC were harvested, washed with phosphate buffered saline (PBS), counted on a Coulter Z1 particle counter (Beckman-Coulter, Miami, Fla.) and resuspended to a concentration of $1 \times 10^7$/mL. The cells were incubated for 30 minutes with mouse anti-human CD8 biotin (Caltag, Burlingame, Calif.) at recommended concentration of 5 microliters for $1 \times 10^6$ cells. After incubation with the primary antibody, the cells were washed with PBS and incubated for 30 minutes with one-microgram/$1 \times 10^6$ cells of either streptavidin-Alexa Fluor®750-Compound 6-R-Phycoerythrin or streptavidin-R-PE-Cy 5.5 (Caltag, Burlingame, Calif.) and 5 microliters of anti-CD4, mouse $IgG_1$, monoclonal 289-14120, Alexa Fluor®488 (Molecular Probes, Inc., Eugene, Oreg.). The cells were washed with PBS, centrifuged, and resuspended with 400 microliters of PBS. The samples were analyzed on a Coulter Elite flow cytometer (Beckman-Coulter, Miami, Fla.) exciting with the 488-nm line of an argon ion laser, collecting the emission with a 575/20 nm bandpass and 710/20 nm bandpass emission filters and 690 long pass dichroic filter. Using a FSC versus SSC dot plot a lymphocyte gate was set and the fluorescence in PMT 4 and PMT 5 was measured. The data was acquired and analyzed using Expo 32 software version 1.2 software. The data was displayed graphically using Excel. Single color controls were used to determine the percent compensation needed for dual color samples.

Example 13

Energy Transfer Pair (Alexa Fluor®680-R-Phycoerythrin) and Compound 6 Conjugated to Streptavidin Used to Detect CD4 on Human Peripheral Blood Mononuclear Cells (PBMC)

Figure 4A:
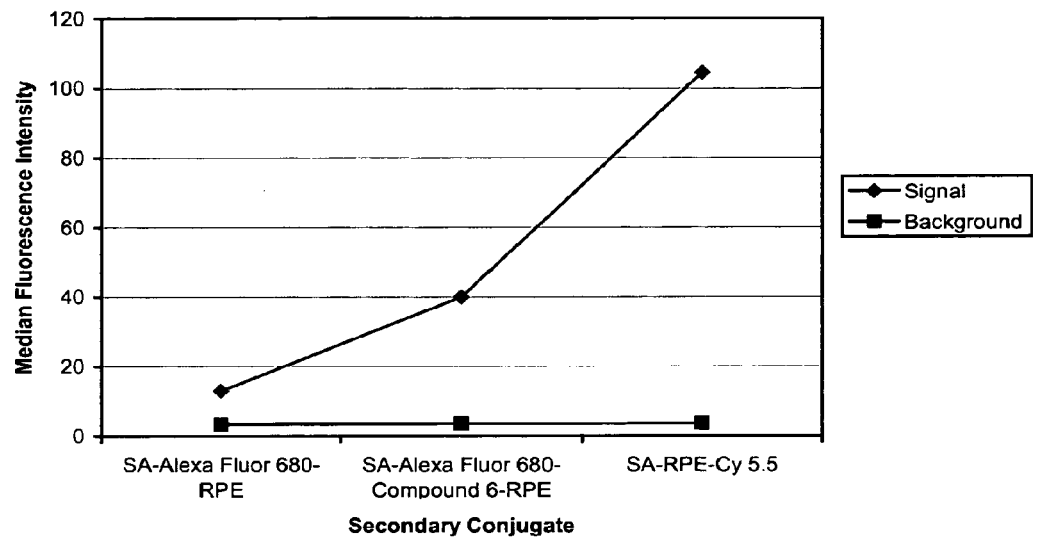
FIG. 4A, FIG. 4B: Shows the fluorescence intensity (FIG. 4A) of three streptavidin conjugates, Alexa Fluor 680-R-PE, Alexa Fluor 680-Compound 6-R-PE and R-PE-Cy 5.5 (CalTag) and the compensation required to obtain the signal (FIG. 4B) when detecting CD4 on peripheral blood mononuclear cells (PBMC) using anti-CD4-biotin antibodies. See, Example 13.
Figure 4B:
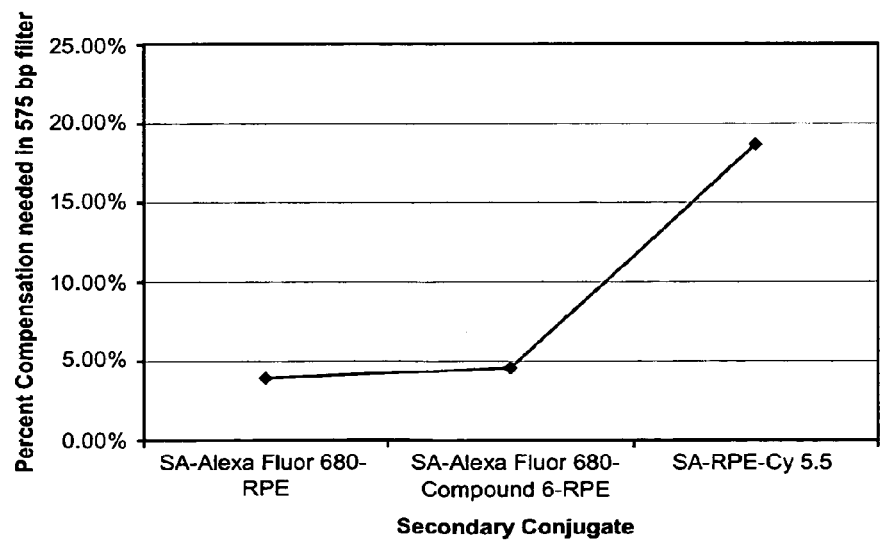

Human Peripheral Blood was drawn into a Cell Preparation Tube (Becton Dickinson, Franklin Lakes, N.J.). Human PBMC were harvested, washed with phosphate buffered saline (PBS), counted on a Coulter Z1 particle counter (Beckman-Coulter, Miami, Fla.) and resuspended to a concentration of $1 \times 10^7$/mL. The cells were incubated for 30 minutes with mouse anti-human CD4 biotin (Caltag, Burlingame, Calif.) at recommended concentration of 0.06 µg for $1 \times 10^6$ cells. After incubation with the primary antibody, the cells were washed with PBS and incubated for 30 minutes with one-microgram/$1 \times 10^6$ cells of either streptavidin-Alexa Fluor®680-Compound 6-R-Phycoerythrin or streptavidin-R-PE-Cy 5.5 (Caltag, Burlingame, Calif.) conjugates and 5 microliters of anti-CD8, mouse $IgG_1$, monoclonal 289-14120, Alexa Fluor®488 (Molecular Probes, Inc., Eugene, Oreg.). The cells were washed with PBS, centrifuged, and resuspended with 400 microliters of PBS. The samples were analyzed on a Coulter Elite flow cytometer (Beckman-Coulter, Miami, Fla.) exciting with the 488-nm line of an argon ion laser, collecting the emission with a 575/20 nm bandpass and 710/20 nm bandpass emission filters and 690 long pass dichroic filter. Using a FSC versus SSC dot plot a lymphocyte gate was set and the fluorescence in PMT 4 and PMT 5 was measured. The data was acquired and analyzed using Expo 32 software version 1.2 software. The data was analyzed for fluorescence and compensation using Win List 3D version 5.0 (Verity Software, Topsham, Me.). The data was displayed graphically using Excel. Single color controls were used to determine the percent compensation needed for dual color samples. See FIG. 4.

Example 14

Preparation of Compound 8

Compound 6 is treated with one equivalent of N-(2-aminoethyl)maleimide, trifluoroacetic acid in DMF in the presence of 3 equivalents of triethylamine to produce the product.

Compound 8

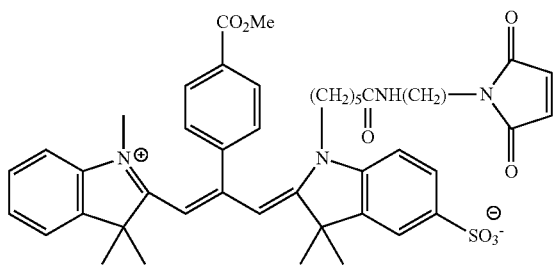

Example 15

Preparation of Compound 9

To a solution of compound 6 in DMF at room temperature, 1.5 equivalent of anhydrous hydrazine is added to generate the product.

Compound 9

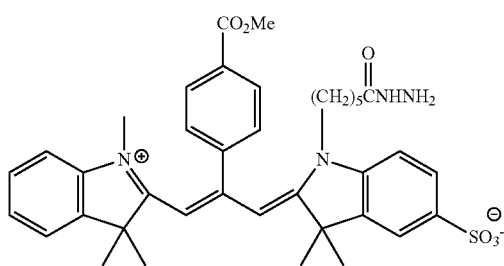

Example 16

Preparation of Compound 10

Compound 5 is hydrolyzed with dilute aqueous sodium hydroxide in methanol and the resulting carboxylic acid is transformed into the corresponding succinimidyl ester Compound 10

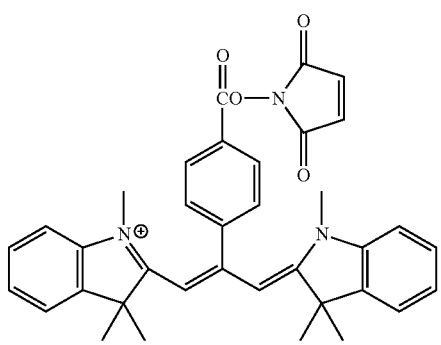

Example 17

Preparation of Compound 11

Compound 10 is reacted with N-tBoc-1,2-ethylenediamine hydrochloride in DMF in the presence of triethylamine to yield the protected amine. The protecting tBoc group is then removed with TFA to yield the corresponding amine trifluoroacetic acid salt.

Compound 11

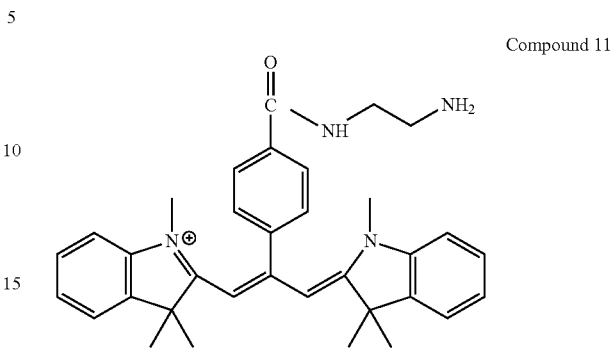

Example 18

Quenching the Fluorescence of Nucleic Acid Stains Bound to Oligonucleotides in Solution Eighteen-base oligonucleotide conjugates of present cyanine quencher dyes are prepared using standard methods. Essentially, a primary amine is synthetically incorporated on the 5' end of the oligonucleotide as a phosphoramidite and reacted subsequently with a succinimidyl ester quencher dye (Compound 6). Alternatively, conjugates are prepared by reacting a quencher maleimide with a thiol that has been incorporated via a phosphoramidite. Conjugates are purified by reverse phase HPLC. Solutions containing 200 ng/mL of each of the conjugates are prepared in 10 mM Tris, pH 7.8, 1 mM EDTA, containing 0.5 µM nucleic acid stain and the fluorescence of the mixture is measured. As a control, the fluorescence of the nucleic acid stain bound to an equal concentration of unconjugated oligonucleotide of the same sequence is measured. The degree of quenching is defined as the fluorescence of 0.5 µM of the nucleic acid stain-bound conjugate minus the fluorescence of the same concentration of the nucleic acid stain alone. All dyes are able to quench the fluorescence of the nucleic acid stains, provided that the emission of the donor dye shows some overlap with the absorption of the quencher dye. Quenchers with long wavelength absorption maxima are especially superior for quenching nucleic acid stains with long wavelength emissions.

Example 19

Quenching Nucleic Acid Stains Bound to Oligonucleotides in Gels or in Capillary Electrophoresis Oligonucleotide primers labeled with present cyanine quencher dyes, prepared as described above (Example 18), are separated by electrophoresis in polyacrylamide or agarose gels, or are separated in capillary electrophoresis, or using microfluidic methods, along with unlabeled primers and PCR products or other products of primer extension. The gels are then stained with an appropriate nucleic acid gel stain, such as ethidium bromide, SYBR Green I stain, SYBR Green II stain, a red fluorescent SYTO stain, SYBR Gold stain, SYTO blue stain, SYTO green stain, or SYTO orange stain. Alternatively, the capillary electrophoresis is performed in the presence of the stain, using standard methods. Primers labeled with the quencher dyes are essentially nonfluorescent in the presence of the fluorescent nucleic acid stain, and thus do not contribute appreciably to the staining pattern in the gel. This simplified pattern facilitates automated gel or capillary electrophoresis analysis. Similarly quenched primers or ligation monomers can be eliminated from the staining pattern in a ligation assay containing one labeled and one unlabeled oligonucleotide, or a telomerase assay. Primer dimers with quenchers on both 5' ends are also not detected by fluorescence because their fluorescence is essentially fully quenched, so that even if they are abundant they do not obscure signals due to short amplification products.

Example 20

Quenching Oligonucleotide Primers in PCR Reactions

PCR reactions are prepared, using oligonucleotide primers labeled with a present cyanine quencher compound. SYBR Green I stain is included at a dilution of 1:50,000 of the commercially available stock solution, or PICOGREEN reagent is added to the reaction after PCR is completed at a final concentration of 0.8 µM, and the fluorescence of the solution is measured. If SYBR Green I stain is included in the reaction, then the reaction can be monitored in real time, using an appropriate instrument, such as the LIGHTCYCLER (Roche) or the GENEAMP 9700 (Perkin Elmer). The background fluorescence in reactions containing quenched primers is lower than that observed in those containing unlabeled primers, and in addition, primer dimers do not contribute to the product signal. Other stains, such as YOYO-1 or OLIGREEN reagent, are added to the solution after PCR with the same results. Other stains, such as YO-PRO-1, are added to the solution prior to or during PCR with essentially the same results.

The preceding examples can be repeated with similar success by substituting the specifically described quenching compounds and energy transfer pairs of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

What is claimed is:

1. A compound having the formula:

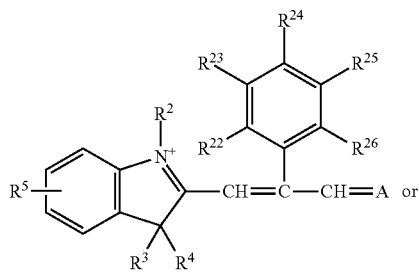

or

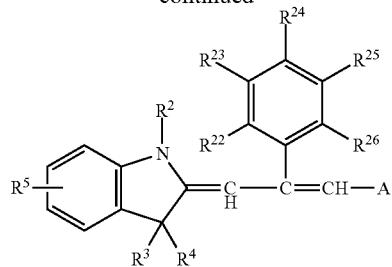

wherein $R^2$ is alkyl, substituted, alkyl, alkoxy, substituted alkoxy, sulfoalkyl, substituted sulfoalkyl, aminoalkyl, substituted aminoalkyl, reactive group, carrier molecule, or solid support;

$R^3$ is alkyl, substituted alkyl, sulfoalkyl, reactive group, carrier molecule, or solid support;

$R^4$ is alkyl, substituted alkyl, sulfoalkyl, reactive group, carrier molecule, or solid support; or $R^3$ and $R^4$ taken together form a 5- or 6-membered saturated ring or a substituted 5- or 6-membered saturated ring;

each $R^5$ is independently hydrogen, alkyl, substituted alkyl, alkoxy, substituted alkoxy, fused benzene, substituted fused benzene, trifluoromethyl, sulfoalkyl, substituted sulfoalkyl, aminoalkyl, substituted aminoalkyl, halogen, reactive group, carrier molecule, or solid support;

$R^{22}$, $R^{23}$, $R^{24}$, $R^{25}$ and $R^{26}$ are independently hydrogen, alkyl, substituted alkyl, alkoxy, substituted alkoxy, amino, substituted amino, aminoalkyl, substituted aminoalkyl, hydroxyl, halogen, thioether, carbonyl, substituted carbonyl, sulfo, substituted sulfo, sulfoalkyl, reactive group, carrier molecule, or solid support; or a member independently selected from $R^{22}$ in combination with $R^{23}$;

$R^{23}$ in combination with $R^{24}$;

$R^{24}$ in combination with $R^{25}$; and $R^{25}$ in combination with $R^{26}$;

together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl; and A is

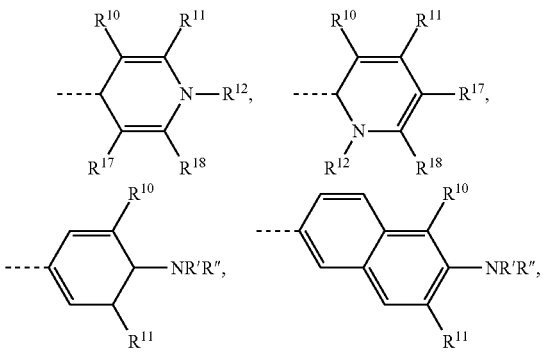

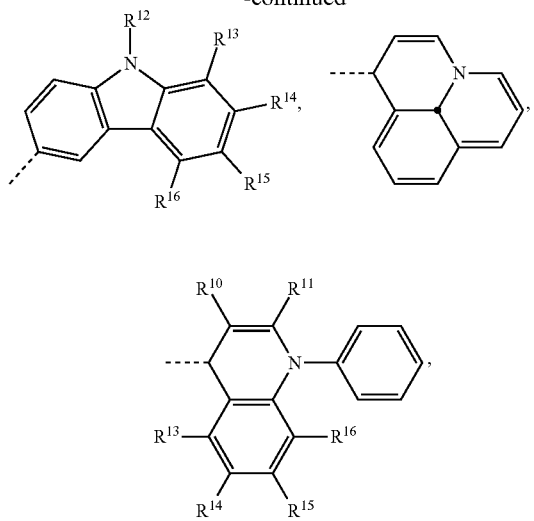

R$^{12}$ is alkyl, substituted, alkyl, alkoxy, substituted alkoxy, sulfoalkyl, substituted sulfoalkyl, aminoalkyl, substituted aminoalkyl, a substituted or unsubstituted aromatic, heteroaromatic, cyclic or heterocyclic moiety, reactive group, carrier molecule, or solid support;

R$^{10}$, R$^{11}$, R$^{13}$, R$^{14}$, R$^{15}$, R$^{16}$, R$^{17}$ and R$^{18}$ are independently hydrogen, alkyl, substituted alkyl, alkoxy, substituted alkoxy, sulfo, substituted sulfo, sulfoalkyl, substituted sulfoalkyl, amino, substituted amino, aminoalkyl, substituted aminoalkyl, trifluoromethyl, halogen, reactive group, carrier molecule, or solid support; or a member independently selected from
R$^{10}$ in combination with R$^{11}$;
R$^{11}$ in combination with R$^{13}$;
R$^{13}$ in combination with R$^{14}$;
R$^{14}$ in combination with R$^{15}$;
R$^{15}$ in combination with R$^{16}$;
R$^{11}$ in combination with R$^{17}$; and
R$^{17}$ in combination with R$^{18}$;
together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl; or
a member independently selected from
R$^{12}$ in combination with R$^{16}$;
R$^{12}$ in combination with R$^{18}$;
R$^{12}$ in combination with R$^{11}$;
R$^{10}$ in combination with R';
R$^{11}$ in combination with R"; or
R' in combination with R";
together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl; and
R' and R" are hydrogen, alkyl or aminoalkyl.

2. The compound according to claim 1, wherein the reactive group, solid support and carrier molecule independently comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

3. The compound according to claim 1, wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol or a photoactivatable group.

4. The compound according to claim 1, wherein the reactive group is carboxylic acid, succinimidyl ester of a carboxylic acid, hydrazide, amine or a maleimide.

5. The compound according to claim 1, wherein the carrier molecule is an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus.

6. The compound according to claim 1, wherein the carrier molecule is an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

7. The compound according to claim 1, wherein the solid support is a microfluidic chip, a silicon chip, a microscope slide, a microplate well, a silica gel, a polymeric membrane, a particle, a derivatized plastic film, a glass bead, cotton, a plastic bead, an alumina gel, a polysaccharide, polyvinylchloride, polypropylene, polyethylene, nylon, latex bead, magnetic bead, paramagnetic bead, or superparamagnetic bead.

8. The compound according to claim 1, wherein the solid support is Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

9. A composition comprising;
a) a luminescent donor molecule;
b) a luminescent acceptor molecule; and
c) a compound that is non-fluorescent acceptor molecule, wherein the compound has the formula according to claim 1.

10. A method for absorbing residual energy from an energy donor molecule during energy transfer between a luminescent donor molecule and a luminescent acceptor molecule, wherein the method comprises:
a) covalently bonding a luminescent donor molecule to a luminescent acceptor molecule to prepare an energy transfer pair;
b) covalently bonding a compound to the energy transfer pair to prepare a quencher labeled energy transfer pair, wherein the compound has the formula:

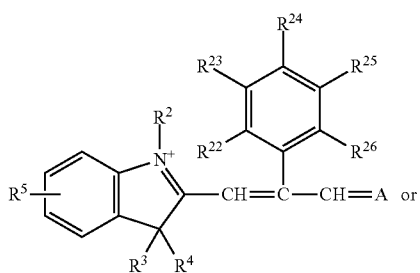

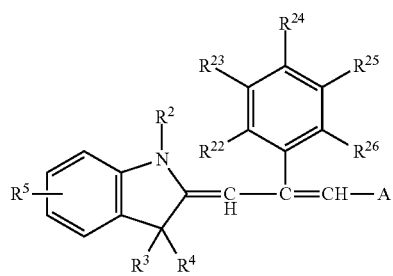

wherein $R^2$ is alkyl, substituted, alkyl, alkoxy, substituted alkoxy, sulfoalkyl, substituted sulfoalkyl, aminoalkyl, substituted aminoalkyl, reactive group, carrier molecule, or solid support;

$R^3$ is alkyl, substituted alkyl, sulfoalkyl, reactive group, carrier molecule, or solid support;

$R^4$ is alkyl, substituted alkyl, sulfoalkyl, reactive group, carrier molecule, or solid support; or $R^3$ and $R^4$ taken together form a 5- or 6-membered saturated ring or a substituted 5- or 6-membered saturated ring;

each $R^5$ is independently hydrogen, alkyl, substituted alkyl, alkoxy, substituted alkoxy, fused benzene, substituted fused benzene, trifluoromethyl, sulfoalkyl, substituted sulfoalkyl, aminoalkyl, substituted aminoalkyl, halogen, reactive group, carrier molecule, or solid support;

$R^{22}$, $R^{23}$, $R^{24}$, $R^{25}$ and $R^{26}$ are independently hydrogen, alkyl, substituted alkyl, alkoxy, substituted alkoxy, amino, substituted amino, aminoalkyl, substituted aminoalkyl, hydroxyl, halogen, thioether, carbonyl, substituted carbonyl, sulfo, substituted sulfo, sulfoalkyl, reactive group, carrier molecule, or solid support; or a member independently selected from $R^{22}$ in combination with $R^{23}$;

$R^{23}$ in combination with $R^{24}$;

$R^{24}$ in combination with $R^{25}$; and $R^{25}$ in combination with R26;

together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl; and A is

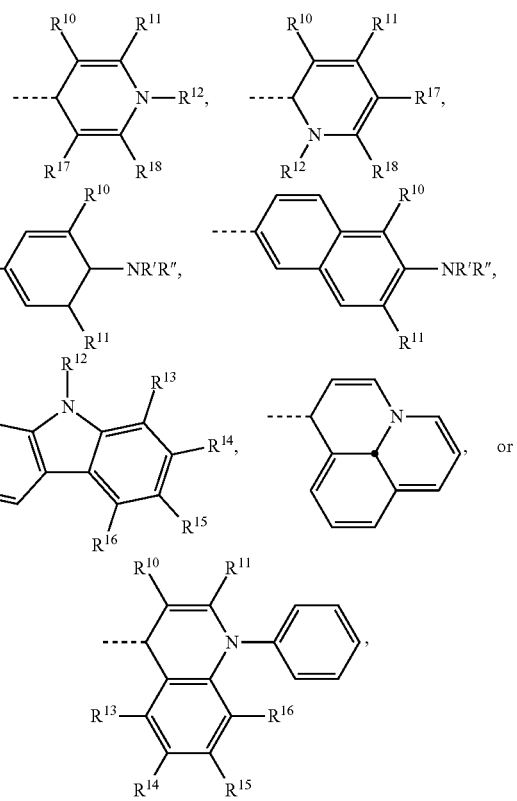

$R^{12}$ is alkyl, substituted, alkyl, alkoxy, substituted alkoxy, sulfoalkyl, substituted sulfoalkyl, aminoalkyl, substituted aminoalkyl, a substituted or unsubstituted aromatic, heteroaromatic, cyclic or heterocyclic moiety, reactive group, carrier molecule, or solid support;

$R^{10}$, $R^{11}$, $R^{13}$, $R^{14}$, $R^{15}$, $R^{16}$, $R^{17}$ and $R^{18}$ are independently hydrogen, alkyl, substituted alkyl, alkoxy, substituted alkoxy, sulfo, substituted sulfo, sulfoalkyl, substituted sulfoalkyl, amino, substituted amino, aminoalkyl, substituted aminoalkyl, trifluoromethyl, halogen, reactive group, carrier molecule, or solid support; or a member independently selected from $R^{10}$ in combination with $R^{11}$;

$R^{11}$ in combination with $R^{13}$;

$R^{13}$ in combination with $R^{14}$;

$R^{14}$ in combination with $R^{15}$;

$R^{15}$ in combination with $R^{16}$;

$R^{11}$ in combination with $R^{17}$; and $R^{17}$ in combination with $R^{18}$;

together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl; or a member independently selected from $R^{12}$ in combination with $R^{16}$;

$R^{12}$ in combination with $R^{18}$, $R^{12}$ in combination with $R^{11}$;

$R^{10}$ in combination with R';

R[11] in combination with R"; or

R' in combination with R";

together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl; and R' and R" are hydrogen, alkyl or aminoalkyl;

c) covalently bonding the quencher labeled energy transfer pair to a carrier molecule to prepare a ternary labeled carrier molecule; and d) illuminating the ternary carrier molecule with an appropriate wavelength wherein fluorescence from the luminescent donor molecule is accepted by the luminescent acceptor molecule and the residual fluorescence from the luminescent donor molecule is accepted by the quenching compound whereby the residual energy is absorbed during energy transfer between a luminescent donor molecule and a luminescent acceptor molecule.

11. A method for detecting the presence or absence of an analyte in a sample, wherein the method comprises:

a) contacting the sample with a composition to prepare a labeled sample, wherein the composition comprises a carrier molecule, a luminescent donor molecule, a luminescent acceptor molecule and a compound having the formula according to claim 1;

b) incubating the labeled sample for a sufficient amount of time for the carrier molecule to associate with the analyte to form an incubated sample;

c) illuminating the incubated sample with an appropriate wavelength to form an illuminated sample; and d) observing the illuminated sample, whereby the presence or absence of the analyte in the sample is detected.

12. A kit for detecting a ligand in a sample, wherein the kit comprises a composition comprising a carrier molecule, a luminescent donor molecule, a luminescent acceptor molecule, and a non-fluorescent acceptor molecule having the formula:

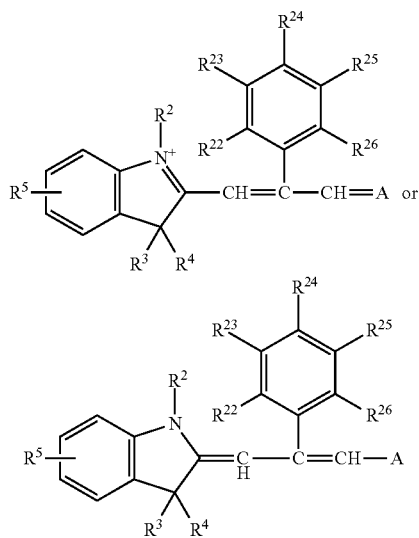

wherein $R^2$ is alkyl, substituted, alkyl, alkoxy, substituted alkoxy, sulfoalkyl, substituted sulfoalkyl, aminoalkyl, substituted aminoalkyl, reactive group, carrier molecule, or solid support;

$R^3$ is alkyl, substituted alkyl, sulfoalkyl, reactive group, carrier molecule, or solid support;

$R^4$ is alkyl, substituted alkyl, sulfoalkyl, reactive group, carrier molecule, or solid support; or $R^3$ and $R^4$ taken together form a 5- or 6-membered saturated ring or a substituted 5- or 6-membered saturated ring;

each $R^5$ is independently hydrogen, alkyl, substituted alkyl, alkoxy, substituted alkoxy, fused benzene, substituted fused benzene, trifluoromethyl, sulfoalkyl, substituted sulfoalkyl, aminoalkyl, substituted aminoalkyl, halogen, reactive group, carrier molecule, or solid support;

$R^{22}$, $R^{23}$, $R^{24}$, $R^{25}$ and $R^{26}$ are independently hydrogen, alkyl, substituted alkyl, alkoxy, substituted alkoxy, amino, substituted amino, aminoalkyl, substituted aminoalkyl, hydroxyl, halogen, thioether, carbonyl, substituted carbonyl, sulfo, substituted sulfo, sulfoalkyl, reactive group, carrier molecule, or substituted solid support; or a member independently selected from $R^{22}$ in combination with $R^{23}$;

$R^{23}$ in combination with $R^{24}$;

$R^{24}$ in combination with $R^{25}$; and $R^{25}$ in combination with $R^{26}$;

together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl; and A is

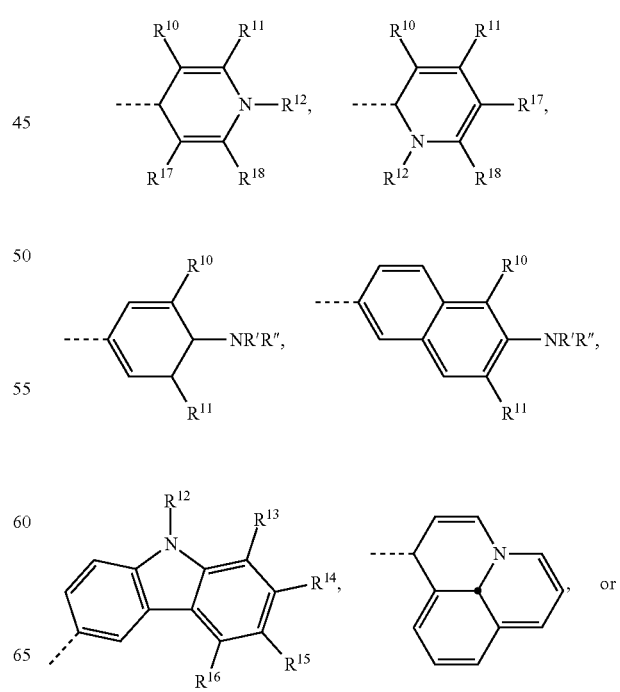

-continued

[Structure: quinoline-like ring system with substituents $R^{10}$, $R^{11}$, $R^{13}$, $R^{14}$, $R^{15}$, $R^{16}$ and N-phenyl group]

$R^{12}$ is alkyl, substituted, alkyl, alkoxy, substituted alkoxy, sulfoalkyl, substituted sulfoalkyl, aminoalkyl, substituted aminoalkyl, a substituted or unsubstituted aromatic, heteroaromatic, cyclic or heterocyclic moiety, reactive group, carrier molecule, or solid support;

$R^{10}$, $R^{11}$, $R^{13}$, $R^{14}$, $R^{15}$, $R^{16}$, $R^{17}$ and $R^{18}$ are independently hydrogen, alkyl, substituted alkyl, alkoxy, substituted alkoxy, sulfo, substituted sulfo, sulfoalkyl, substituted sulfoalkyl, amino, substituted amino, aminoalkyl, substituted aminoalkyl, trifluoromethyl, halogen, reactive group, carrier molecule, or solid support; or a member independently selected from $R^{10}$ in combination with $R^{11}$;
$R^{11}$ in combination with $R^{13}$;
$R^{13}$ in combination with $R^{14}$;
$R^{14}$ in combination with $R^{15}$;
$R^{15}$ in combination with $R^{16}$;
$R^{11}$ in combination with $R^{17}$; and
$R^{17}$ in combination with $R^{18}$;

together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl; or a member independently selected from $R^{12}$ in combination with $R^{16}$;
$R^{12}$ in combination with $R^{18}$;
$R^{12}$ in combination with $R^{11}$;
$R^{10}$ in combination with R';
$R^{11}$ in combination with R"; or
R' in combination with R";

together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl; and R' and R" are hydrogen, alkyl or aminoalkyl.

13. The kit according to claim 12, further comprising instructions for detecting the ligand.

14. A kit for labeling a carrier molecule, wherein the kit comprises: a non-fluorescent compound, wherein the compound has the formula according to claim 1.

* * * * *